(12) United States Patent
Althoff et al.

(10) Patent No.: US 7,083,918 B2
(45) Date of Patent: Aug. 1, 2006

(54) BACTERIAL SMALL-MOLECULE THREE-HYBRID SYSTEM

(75) Inventors: Eric A. Althoff, New York, NY (US); Virginia W. Cornish, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 330 days.

(21) Appl. No.: 10/132,039

(22) Filed: Apr. 24, 2002

(65) Prior Publication Data

US 2003/0203471 A1   Oct. 30, 2003

(51) Int. Cl.
*C12Q 1/68* (2006.01)
*G01N 33/53* (2006.01)
*G01N 33/554* (2006.01)
*G01N 33/567* (2006.01)
*G01N 33/573* (2006.01)

(52) U.S. Cl. .......................... 435/6; 435/7.1; 435/7.2; 435/7.32; 435/7.4

(58) Field of Classification Search .................. 435/6, 435/7.1, 7.2, 7.32, 7.4
See application file for complete search history.

(56) References Cited

U.S. PATENT DOCUMENTS

| | | | |
|---|---|---|---|
| 5,194,594 | A | 3/1993 | Khawli et al. |
| 5,314,817 | A | 5/1994 | Schultz |
| 5,468,614 | A | 11/1995 | Fields et al. |
| 5,736,343 | A | 4/1998 | Landry |
| 5,925,523 | A | 7/1999 | Dove et al. |
| 5,928,868 | A * | 7/1999 | Liu et al. ..................... 435/6 |
| 6,030,785 | A | 2/2000 | Katze et al. |
| 6,200,759 | B1 | 3/2001 | Dove et al. |

FOREIGN PATENT DOCUMENTS

| | | |
|---|---|---|
| EP | 0742015 | 11/1996 |
| WO | 9731113 | 8/1997 |
| WO | 9813353 | 4/1998 |
| WO | 9910508 | 3/1999 |
| WO | 9910510 | 3/1999 |
| WO | 9630540 | 10/1999 |
| WO | 0153355 | 7/2001 |
| WO | WO0259272 | 2/2003 |
| WO | WO0360073 | 11/2003 |
| WO | WO2004042345 | 9/2004 |

OTHER PUBLICATIONS

Cornish, Virginia W. et al., "Dexamethasone-Methotrexate: An Efficient Chemical Inducer Of Protein Dimerization In Vivo," *Abstracts of Papers American Chemical Society*, vol. 219, No. 1-2, p. BIOL 124 (2000).
Cornish, Virginia W. et al., "Synthesis of Dexamethasone-Methotrexate CIDS With Variable Linkers," *Book of Abstracts*, American Chemical Society, 219th ACS National Meeting, San Francisco, CA, p. CHED 401 (Mar. 26-30, 2000).
Griffith, E.C. et al. "Yeast Three-Hybrid System for Detecting Ligand-Receptor Interactions," *Methods in Enzymology*, vol. 328, pp. 89-103 (2000).
Dove et al., (1997) "Activation of Prokaryotic Transcription Through Arbitrary Protein-Protein Contacts" *Nature* 386:627-630 ; and.
Filman et al., (1982) "Crystal Structures of *Escherichia coli* and *Lactobacillus casei* Dihydrofolate Reductase Refined at 1.7 Å Resolution", *The Journal of biological Chemistry* 257(22): 13663-13672.
Amara, J.F. et al. A Versatile Synthetic Dimerizer for the Regulation of Protein-Protein Interactions, *Proc. Natl. Acad. Sci. USA*, 1997, 94, 10618-10623 (Exhibit 1).
Austin DJ, et al. Proximity versus allostery: the role of regulated protein dimerization in biology. 1994. Chem Biol. 1(3): 131-6 (Exhibit 13).
Belshaw PJ, et al. Controlling protein association and subcellular localization with a synthetic ligand that induces heterodimerization of proteins. 1996. Proc. Natl Acad Sci USA 93(10):4604-7 (Exhibit 14).
Belshaw PJ, et al. Controlling programmed cell death with a cyclophilin-cyclosporin-based chemical inducer of dimerization. 1996. Chem. Biol. 3:731-738 (Exhibit 15).
Choi J, et al. Structure of the FKBP-12-Rapamycin complex interacting with the binding domain of human FRAP. 1996. Science 273(5272):239-42 (Exhibit 16).
DeGrado WF, et al. Screening, selection and design: standing at the crossroads in three dimensions. 1997. Current Opinion in Structural Biology 7:455-456 (Exhibit 17.)

(Continued)

*Primary Examiner*—Mark Navarro
(74) *Attorney, Agent, or Firm*—John P. White, Esq.; Cooper & Dunham LLP

(57) ABSTRACT

A transgenic bacterial cell comprising
(a) a dimeric small molecule which comprises a first moiety known to bind a first receptor domain covalently linked to a second moiety known to bind a second receptor domain;
(b) nucleotide sequences which upon transcription encode
  i) a first fusion protein comprising the first receptor domain, and
  ii) a second fusion protein comprising the second receptor domain; and
(c) a reporter gene wherein expression of the reporter gene is conditioned on the proximity of the first fusion protein to the second fusion protein. The cell is also adapted for use in a method for identifying a molecule that binds to a known target in a bacterial cell from a pool of candidate molecules, and a method for identifying an unknown target receptor to which a molecule is capable of binding in a bacterial cell. Also described are compounds and kits for carrying out the methods.

42 Claims, 5 Drawing Sheets

OTHER PUBLICATIONS

Diver SR, et al. Single-step synthesis of cell-permeable protein dimerizers that activate signal transduction and gene expression. 1997. J. Am. Chem. Soc. 119: 5106-5109 (Exhibit 18).

Ho SN, et al. Dimeric ligands define a role for transcriptional activation domains in reinitiation. 1996. Nature. 382(6594):822-6 (Exhibit 19).

Holsinger LJ, et al. Signal transduction in T lymphocytes using a conditional allele of Sos. 1995. Proc. Natl. Acad. Sci. USA 92:9810-9814 (Exhibit 20).

Hung DT, et al. Understanding and controlling the cell cycle with natural products. 1996. Chem. Biol. 3:623-639 (Exhibit 21).

Klemm JD, et al. Dimerization as a regulatory mechanism in signal transduction. 1998. Annu. Rev. Immunol. 16:569-92 (Exhibit 22).

Liberles SD, et al. Inducilble gene expression and protein translocation using nontoxic ligands identified by a mammalian three-hybrid screen. 1997. Proc. Natl. Acad. Sci. USA 94(15):7825-7830 (Exhibit 23).

Licitra EJ, et al. A three-hybrid system for detecting small ligand-protein receptor interactions. 1996. Proc. Natl. Acad. Sci. USA 98:12817-12821 (Exhibit 24).

Pedersen H, et al. A method for directed evolution and functional cloning of enzymes. 1998. Proc. Natl. Acad. Sci. USA 95:10523-10528 (Exhibit 25).

Pruschy MN, et al. Mechanistic studies of a signaling pathway activated by the organic dimerizer FK1012. 1994. Cbem. Biol. 1:163-172 (Exhibit 26).

Schreiber SL. Chemical genetics resulting from a passion for synthetic organic chemistry. 1998. Bioorganic & Medicinal Chemistry 6:1127-1152 (Exhibit 27).

Spencer DM, et al. Controlling signal transduction with synthetic ligands. 1993. Science 262(5136):1019-1024 (Exhibit 28).

Spencer DM, et al. Functional analysis of Fas signaling in vivo using synthetic inducers of dimerization. 1996. Curr Biol. 6(7):839-47 (Exhibit 29).

Spencer DM, et al. A general strategy for producing conditional alleles of Src-like tyrosine kinases. 1995. Proc. Natl. Acad. Sci. 92:9805-9809 (Exhibit 30).

Stockwell BR, et al. TGF-beta-signaliung with small molecule FKBP12 antagonists that bind myristoylated FKBP12-TGF-beta type 1 receptor fusion proteins. 1998. Chem Biol. 5(7):385-95 (Exhibit 31).

Stockwell BR, et al. Probing the role of homomeric and heteromeric receptor interactions in TGF-beta signaling using small molecule dimerizers. 1998. Curr Biol 8(13):761-70 (Exhibit 32).

Winkler T., et al. Confocal fluorescence coincidence analysis: An approach to ultra high-throughput screening. 1998 Proc. Natl. Acad. Sci. USA 96:1375-1378 (Exhibit 33).

Yang, J., et al. Small-molecule control of insulin and PDGF receptor signaling and the role of membrane attachment. 1997 Curr. Biol. 8:11-18 (Exhibit 34).

Zlokarnik G, et al. Quatitation of tranmscription and clonal selection of single living cells with beta-lactamase as reporter. 1998, Science 279(5347):84-8 (Exhibit 35).

Search Report dated May 14, 2001 corresponding PCT International Application No. PCT/US01/02285 (Exhibit 36).

Lin, H., et al. Dexamethasone-Methotrexate: An Efficient Chemical Inducer of Protein Dimerization *In Vivo*. 2000. J.Am.Chem.Soc. 122:4247-4248 (Exhibit 37).

Kopytek, S.J., et al. Chemically Induced Dimerization of Dihydrofolate Reductase by a Homobifunctional Dimer of Methotrexate. 2000. Chem Biol 7:313-321 (Exhibit 38).

Firestine, S.M., et al. Using an AraC-Based three-hybrid system to detect biocatalysts in vivo. 2000. Nature Biotechnology. 18, 544-547 (Exhibit 40).

Pelletier, J.N., et al. Oligomerization domain-directed reassembly of active dihydrofolate reductase from rationally designed fragments. 1998. Proc.Natl. Acad.Sci.USA. 95, 12141-12146 (Exhibit 41).

Ladant, D., Karimova, G. Genetic systems for analyzing protein-protein interactions in bacteria. 2000. Res. Microbiol. 151, 711-720 (Exhibit 42).

Pollack et al., (2002) "Dimerizer-regulated gene expression" *Current Opinion in Biotechnology* 13:459-467.

U.S. Appl. No. 10/056,874, filed Jan. 24, 2002.

U.S. Appl. No. 10/084,388, filed Feb. 25, 2002.

* cited by examiner

A.

B.

SEQUENCE LISTING

```
<160> NUMBER OF SEQ ID NOS: 8

<210> SEQ ID NO 1
<211> LENGTH: 56
<212> TYPE: DNA
<213> ORGANISM: Artificial Sequence
<220> FEATURE:
<223> OTHER INFORMATION: Primer VWC482
```

```
<400> SEQUENCE: 1
acttcaggtg cggccgcagg ctcgggcggc tcgggcggcg gagtgcaggt ggaaac          56

<210> SEQ ID NO 2
<211> LENGTH: 62
<212> TYPE: DNA
<213> ORGANISM: Artificial Sequence
<220> FEATURE:
<223> OTHER INFORMATION: Primer VWC487

<400> SEQUENCE: 2
tgtatcaacg gatccttaat ggtgatggtg atggtgcgag ccgaattctt ccagttttag      60
aa                                                                    62

<210> SEQ ID NO 3
<211> LENGTH: 20
<212> TYPE: DNA
<213> ORGANISM: Artificial Sequence
<220> FEATURE:
<223> OTHER INFORMATION: Primer VWC628

<400> SEQUENCE: 3
ctggctgaac aactggaagc                                                 20

<210> SEQ ID NO 4
<211> LENGTH: 20
<212> TYPE: DNA
<213> ORGANISM: Artificial Sequence
<220> FEATURE:
<223> OTHER INFORMATION: Primer VWC629

<400> SEQUENCE: 4
atataggcgc cagcaaccgc                                                 20

<210> SEQ ID NO 5
<211> LENGTH: 56
<212> TYPE: DNA
<213> ORGANISM: Artificial Sequence
<220> FEATURE:
<223> OTHER INFORMATION: VWC611

<400> SEQUENCE: 5
acttcaggtg cggccgcagg ctcgggcggc tcgggcggcg gagtgcaggt ggaaac          56

<210> SEQ ID NO 6
<211> LENGTH: 64
<212> TYPE: DNA
<213> ORGANISM: Artificial Sequence
<220> FEATURE:
<223> OTHER INFORMATION: Primer VWC612

<400> SEQUENCE: 6
tgtatcaacg gcgcgcctta atggtgatgg tgatggtgcg agccgaattc ttccagtttt      60
agaa                                                                  64

<210> SEQ ID NO 7
<211> LENGTH: 20
<212> TYPE: DNA
<213> ORGANISM: Artificial Sequence
<220> FEATURE:
<223> OTHER INFORMATION: Primer VWC626

<400> SEQUENCE: 7
cccaatgatc ccatgcaatg                                                 20
```

-continued

```
<210> SEQ ID NO 8
<211> LENGTH: 20
<212> TYPE: DNA
<213> ORGANISM: Artificial Sequence
<220> FEATURE:
<223> OTHER INFORMATION: Primer VWC627

<400> SEQUENCE: 8
gcgcttcgtt aatacagatg                                                 20
```

US 7,083,918 B2

BACTERIAL SMALL-MOLECULE THREE-HYBRID SYSTEM

This invention has been made with government support under National Institutes of Health grant GM62867. Accordingly, the U.S. Government has certain rights in the invention.

Throughout this application, various publications are referenced by Arabic numerals in parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

FIELD OF THE INVENTION

This invention relates to the field of identifying protein targets and their corresponding small-molecule drugs and other biomolecules using the techniques of chemically induced dimerization ("CID").

BACKGROUND OF THE INVENTION

Affinity chromatography has long been used to identify the protein targets of small-molecule drugs and other biomolecules. While an essential tool for biochemical research, affinity chromatography can often be labor intensive and time consuming. Recently the yeast three-hybrid assay, a derivative of the two-hybrid assay, was introduced as a straightforward, in vivo alternative to affinity chromatography (1,2). The yeast two-hybrid system relies on the interaction of two fusion proteins to bring about the transcriptional activation of a reporter gene thus identifying protein-protein interactions in an in vivo system (2). The subsequently developed yeast three-hybrid system screens for a small molecule-protein interaction based on the principle that small ligand-receptor interactions underlie many fundamental processes in biology and form the basis for pharmacological intervention of human diseases in medicine (3). In the three-hybrid assay, protein-small-molecule interactions are detected as reconstitution of a transcriptional activator ("TA") and subsequent transcription of a reporter gene (4–7). A dimeric small-molecule ligand bridges the DNA-binding domain ("DBD") of the TA, which is fused to the receptor for one ligand, and the activation domain ("AD") of the TA, which is fused to the receptor for the other ligand. For affinity chromatography applications, one ligand-receptor pair is used as an anchor and the other is the small-molecule-protein interaction being investigated. While the yeast three-hybrid assay is quite powerful, a bacterial equivalent would increase the number of proteins that could be tested by several orders of magnitude because the transformation efficiency and doubling time of $E.\ coli$ is significantly greater than that of $S.\ cerevisiae$. In addition, there may be applications where it is advantageous to test a eukaryotic protein in a prokaryotic environment where many pathways are not conserved.

However, the yeast three-hybrid assay cannot be transferred directly to bacteria. The components of the transcription machinery and the mechanism of transcriptional activation differ significantly between bacteria and yeast. Ligand-receptor pairs often are organism specific because of cell permeability, toxicity, or other interactions with the cellular milieu. Bacterial two-hybrid assays have only begun to be developed in the past few years (8) and to date only initial efforts toward the design of a robust bacterial three-hybrid system have been reported (9, 10). Described below is the first robust small-molecule bacterial three-hybrid system.

SUMMARY OF THE INVENTION

This invention provides a transgenic bacterial cell comprising
  (a) a dimeric small molecule which comprises a first moiety known to bind a first receptor domain covalently linked to a second moiety capable of binding a second receptor domain, wherein the first and second moieties are different;
  (b) nucleotide sequences which upon transcription encode
    i) a first fusion protein comprising the first receptor domain, and
    ii) a second fusion protein comprising the second receptor domain; and
  (c) a reporter gene wherein expression of the reporter gene is conditioned on the proximity of the first fusion protein to the second fusion protein.

This invention also provides a method for identifying a molecule that binds a known target receptor in a bacterial cell from a pool of candidate molecules, comprising:
  (a) forming a dimeric molecule by covalently bonding each molecule in the pool of candidate molecules to a ligand capable of selectively binding to a receptor;
  (b) introducing the dimeric molecule into a bacterial cell culture comprising bacterial cells that express
    a first fusion protein which comprises the known target receptor domain against which the candidate molecule is screened,
    a second fusion protein which comprises the receptor domain to which the ligand selectively binds, and
    a reporter gene wherein expression of the reporter gene is conditioned on the proximity of the first fusion protein to the second fusion protein;
  (c) permitting the dimeric molecule to bind to the first fusion protein and to the second fusion protein, bringing the two fusion proteins into proximity so as to activate the expression of the reporter gene;
  (d) selecting the bacterial cell that expresses the reporter gene; and
  (e) identifying the small molecule that binds the known target receptor.

This invention further provides a method for identifying an unknown target receptor to which a known molecule is capable of binding in a bacterial cell, comprising:
  (a) providing a dimeric molecule having a first ligand which has a specificity for the unknown target receptor covalently bonded to a second ligand capable of selectively binding to a receptor;
  (b) introducing the dimeric molecule into a bacterial cell which expresses
    a first fusion protein which comprises the unknown target receptor domain,
    a second fusion protein which comprises the receptor domain to which the second ligand selectively binds, and
    a reporter gene wherein expression of the reporter gene is conditioned on the proximity of the first fusion protein to the second fusion protein;
  (c) permitting the dimeric molecule to bind to the first fusion protein and to the second fusion protein so as to activate the expression of the reporter gene;

(d) selecting which bacterial cell expresses the unknown target receptor; and (e) identifying the unknown target receptor.

This invention also provides a transgenic bacterial cell comprising
- (a) a dimeric small molecule which comprises a methotrexate moiety covalently linked to a moiety capable of binding a receptor domain;
- (b) nucleotide sequences which upon transcription encode
  - i) a first fusion protein comprising a DHFR domain and a first fragment of an enzyme, and
  - ii) a second fusion protein comprising the receptor domain and a second fragment of the enzyme,
- wherein activity of the enzyme is conditioned on the proximity of the first fragment of the enzyme to the second fragment of the enzyme.

This invention further provides a method for identifying a molecule that binds a known target receptor in a bacterial cell from a pool of candidate molecules, comprising:
- (a) forming a dimeric molecule by covalently bonding each molecule in the pool of candidate molecules to a methotrexate moiety;
- (b) introducing the dimeric molecule into a bacterial cell culture comprising bacterial cells that express
  - a first fusion protein which comprises the known target receptor domain against which the candidate molecule is screened, and a first fragment of an enzyme, and
  - a second fusion protein which comprises a DHFR receptor domain and a second fragment of the enzyme;
- (c) permitting the dimeric molecule to bind to the first fusion protein and to the second fusion protein, bringing the first fragment and the second fragment of the enzyme in to proximity so as to reconstitute the activity of the enzyme;
- (d) selecting the bacterial cell that exhibits the activity of the enzyme; and
- (e) identifying the small molecule that binds the known target receptor.

This invention also provides a method for identifying an unknown target receptor to which a known molecule is capable of binding in a bacterial cell, comprising:
- (a) providing a dimeric molecule having a first ligand which has a specificity for the unknown target receptor covalently bonded to a methotrexate moiety;
- (b) introducing the dimeric molecule into a bacterial cell which expresses
  - a first fusion protein which comprises the unknown target receptor domain, and a first fragment of an enzyme, and
  - a second fusion protein which comprises a DHFR receptor domain and a second fragment of the enzyme;
- (c) permitting the dimeric molecule to bind to the first fusion protein and to the second fusion protein, bringing the first fragment and the second fragment of the enzyme in to proximity so as to reconstitute the activity of the enzyme;
- (d) selecting the bacterial cell that exhibits the activity of the enzyme; and
- (e) identifying the unknown target receptor.

Also provided by this invention is are kits for carrying out the methods.

DETAILED DESCRIPTION OF THE INVENTION

Figure 1:
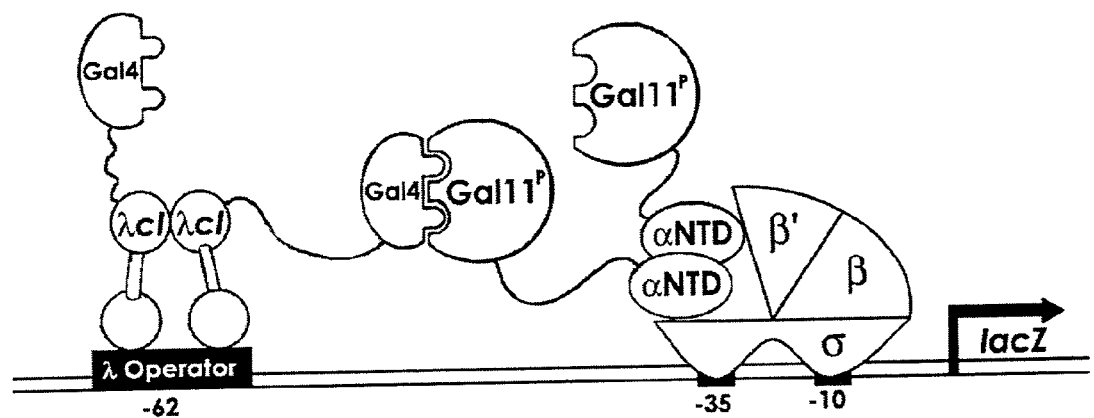
FIG. 1. Bacterial RNA polymerase two- and three-hybrid systems. (A) Dove and Hochschild built a bacterial two-hybrid system based on their observation that λcI-mediated recruitment of RNA polymerase is sufficient to activate gene transcription. The DNA operator of λcI is placed upstream of the RNA polymerase binding site for a lacZ reporter gene. Using the known interaction between the proteins, Gal4 and Gal11$^P$, as a proof of principle, they showed that co-expression of λcI-Gal4 and αNTD-Gal11$^P$ fusion proteins was sufficient to activate transcription of the lacZ gene. λcI binds to its operator and through the binding of Gal4 and Gal11$^P$ is effectively associated with αNTD. αNTD is the N-terminal domain of the α-subunit of RNA polymerase and is used to localize the entire RNA polymerase machinery to the RNA polymerase binding site and thus promote transcription of the lacZ gene. (B) In our bacterial three-hybrid system, the interaction between λcI and αNTD is provided by a heterodimeric small molecule, Mtx-SLF. Mtx-SLF bridges between the fusion proteins, λcI-FKBP12 (the receptor for SLF) and αNTD-DHFR (the receptor for Mtx), activating transcription of the lacZ reporter gene.
Figure 1:
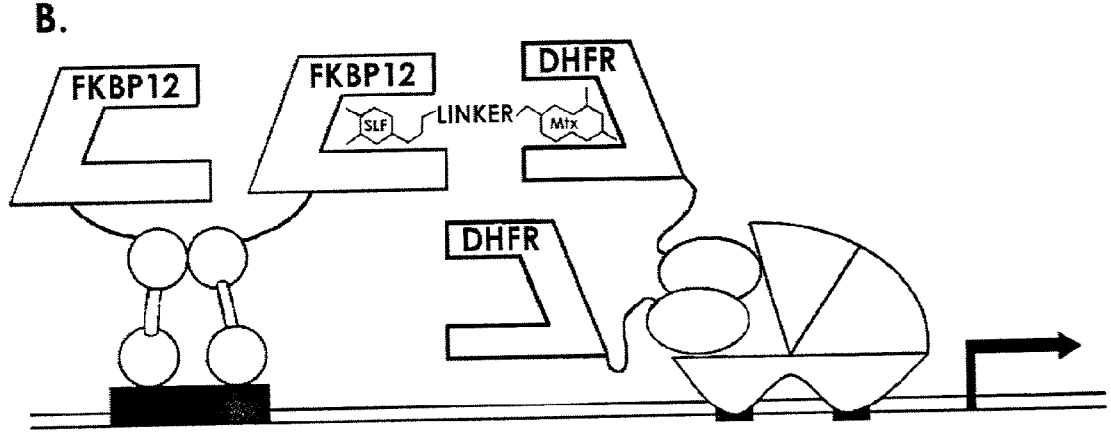

This invention provides a transgenic bacterial cell comprising
(a) a dimeric small molecule which comprises a first moiety known to bind a first receptor domain covalently linked to a second moiety capable of binding a second receptor domain, wherein the first and second moieties are different;
(b) nucleotide sequences which upon transcription encode
   i) a first fusion protein comprising the first receptor domain, and
   ii) a second fusion protein comprising the second receptor domain; and
(c) a reporter gene wherein expression of the reporter gene is conditioned on the proximity of the first fusion protein to the second fusion protein.

The dimeric small molecule may have the formula:

H1—Y—H2 wherein each of H1 and H2 may be the same or different and capable of binding to a receptor which is the same or different with a $IC_{50}$ of less than 100 μM; and Y is a linker which may be present or absent. Each of H1 and H2 can be capable of binding to a receptor with a $IC_{50}$ of less than 10 μM; or with a $IC_{50}$ of less than 1 μM; or with a $IC_{50}$ of less than 100 nM; or with a $IC_{50}$ of less than 10 nM; or with a $IC_{50}$ of less than 1 nM.

Each of H1 and H2 may be a methotrexate moiety, FK506 moiety, an FK506 analog, a tetracycline moiety, or a cephem moiety. In a preferred embodiment, H1 or H2 is a methotrexate moiety. In another preferred embodiment, H1 or H2 is an FK506 analog.

The FK506 analog may have the structure:

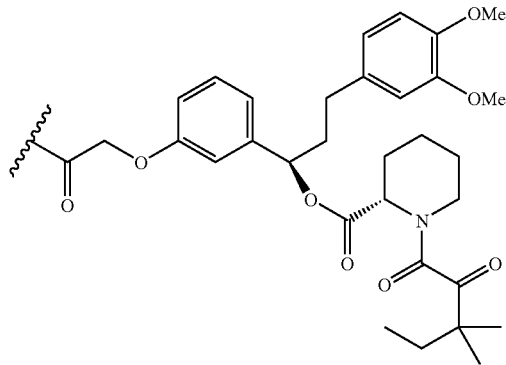

In a specific embodiment, the dimeric small molecule may have the structure:

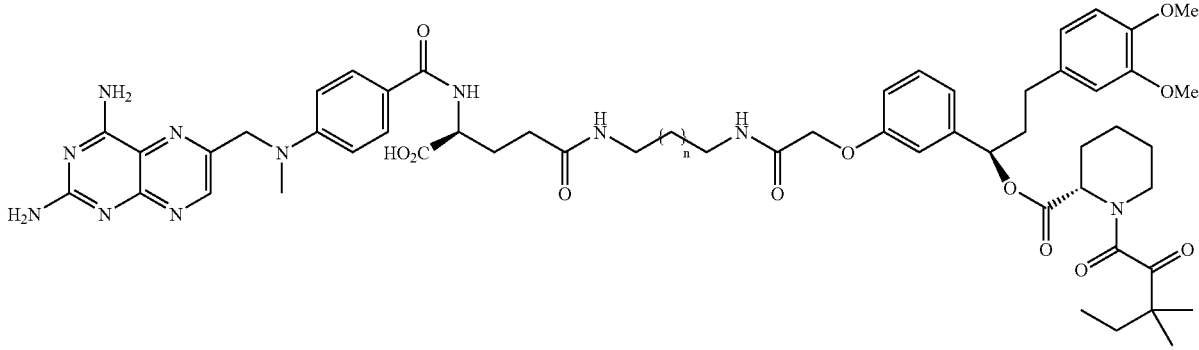

wherein n is an integer from 1 to 20, preferably n is an integer from 2 to 12, more preferably n is an integer from 3 to 9, in a specific embodiment, n is 8.

The first fusion protein can further comprise a DNA binding domain, and the second fusion protein can further comprises a transcription activation domain. Alternatively, the first fusion protein can further comprises a transcription activation domain, and the second fusion protein can further comprises a DNA binding domain.

The transcription activation domain can be αNTD. The DNA-binding domain can be λcI, AraC, LexA, Gal4, or zinc fingers.

The first or the second receptor domain can be that of dihydrofolate reductase ("DHFR"), glucocorticoid receptor, FKBP12, FKBP mutants, tetracycline repressor, or a penicillin binding protein. The DHFR can be the E. coli DHFR ("eDHFR").

In a specific embodiment, the first fusion protein is DHFR-λcI or FKBP12-λcI; and the second fusion protein is DHFR-αNTD or FKBP12-αNTD.

The reporter gene can be Lac Z, araBAD, aadA (spectinomycin resistance), his3, β-lactamase, GFP, luciferase, TetR (tetracyclin resistance), KanR (kanamycin resistance), or Cm (chloramphenicol resistance). In a specific embodiment, the reporter gene is Lac Z.

This invention also provides a transgenic bacterial cell comprising
(a) a dimeric small molecule which comprises a methotrexate moiety covalently linked to a moiety capable of binding a receptor domain;

(b) nucleotide sequences which upon transcription encode
  i) a first fusion protein comprising a DHFR domain, and
  ii) a second fusion protein comprising the receptor domain; and
(c) a reporter gene wherein expression of the reporter gene is conditioned on the proximity of the first fusion protein to the second fusion protein.

The elements of this cell are as defined previously.

This invention also provides a method for identifying a molecule that binds a known target receptor in a bacterial cell from a pool of candidate molecules, comprising:
(a) forming a dimeric molecule by covalently bonding each molecule in the pool of candidate molecules to a ligand capable of selectively binding to a receptor;
(b) introducing the dimeric molecule into a bacterial cell culture comprising bacterial cells that express
  a first fusion protein which comprises the known target receptor domain against which the candidate molecule is screened,
  a second fusion protein which comprises the receptor domain to which the ligand selectively binds, and
  a reporter gene wherein expression of the reporter gene is conditioned on the proximity of the first fusion protein to the second fusion protein;
(c) permitting the dimeric molecule to bind to the first fusion protein and to the second fusion protein, bringing the two fusion proteins into proximity so as to activate the expression of the reporter gene;
(d) selecting the bacterial cell that expresses the reporter gene; and
(e) identifying the small molecule that binds the known target receptor.

In the method, the steps (b)–(e) of the method can be iteratively repeated in the presence of a preparation of random small molecules for competitive binding with the screening molecule so as to identify a molecule capable of competitively binding the known target receptor.

The dimeric molecule in the method can be obtained from a combinatorial library. The dimeric molecule in the method can comprise a ligand capable of selectively binding to a receptor with a $IC_{50}$ of less than 100 μM; or with a $IC_{50}$ of less than 10 μM; or with a $IC_{50}$ of less than 1 μM; or with a $IC_{50}$ of less than 100 nM; or with a $IC_{50}$ of less than 10 nM; or with a $IC_{50}$ of less than 1 nM.

The dimeric molecule in the method can comprises a methotrexate moiety, FK506 moiety, an FK506 analog, a tetracycline moiety, or a cephem moiety. In a specific embodiment, the dimeric molecule comprises a methotrexate moiety. In another specific embodiment, the dimeric molecule comprises an FK506 analog.

The FK506 analog can have has the structure:

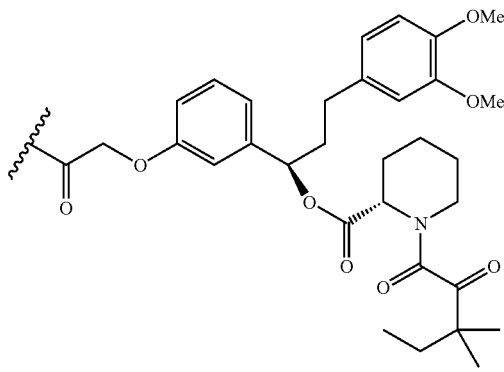

The first fusion protein in the method can further comprise a DNA binding domain, and the second fusion protein further comprises a transcription activation domain. Alternatively, the first fusion protein in the method can further comprise a transcription activation domain, and the second fusion protein further comprises a DNA binding domain.

The transcription activation domain can be αNTD.

The DNA-binding domain can be λcI, AraC, LexA, Gal4, or zinc fingers.

The first or the second fusion protein in the method can comprise a receptor domain of dihydrofolate reductase ("DHFR"), glucocorticoid receptor, FKBP12, FKBP mutants, tetracycline repressor, or a penicillin binding protein. The DHFR can be the E. coli DHFR ("eDHFR").

In the method, the first fusion protein can be DHFR-λcI or FKBP12-λcI. The second fusion protein can be DHFR-αNTD or FKBP12-αNTD.

The reporter gene can be Lac Z, araBAD, aadA, his3, β-lactamase, GFP, luciferase, TetR, KanR, Cm. In a specific embodiment, the reporter gene is Lac Z.

This invention also provides a method for identifying an unknown target receptor to which a known molecule is capable of binding in a bacterial cell, comprising:
(a) providing a dimeric molecule having a first ligand which has a specificity for the unknown target receptor covalently bonded to a second ligand capable of selectively binding to a receptor;
(b) introducing the dimeric molecule into a bacterial cell which expresses
  a first fusion protein which comprises the unknown target receptor domain,
  a second fusion protein which comprises the receptor domain to which the second ligand selectively binds, and
  a reporter gene wherein expression of the reporter gene is conditioned on the proximity of the first fusion protein to the second fusion protein;
(c) permitting the dimeric molecule to bind to the first fusion protein and to the second fusion protein so as to activate the expression of the reporter gene;
(d) selecting which bacterial cell expresses the unknown target receptor; and
(e) identifying the unknown target receptor.

The unknown target receptor is encoded by a DNA from the group consisting of genomicDNA, cDNA and synthetcDNA.

The steps (b)–(e) of the method can be iteratively repeated so as to identify the unkown target receptor.

The other elements of this method are as defined previously.

This invention also provides a kit for identifying a molecule that binds to a known target in a bacterial cell from a pool of candidate molecules, comprising
(a) a host bacterial cell containing a reporter gene that is expressed only when bound to a DNA-binding domain and when in the proximity of a transcription activation domain;
(b) a first vector containing a promoter that functions in the host bacterial cell and a DNA encoding a DNA-binding domain;
(c) a second vector containing a promoter that functions in the host bacterial cell and a DNA encoding a transcription activation domain;
(d) a dimeric small molecule which comprises a moiety that binds to a known receptor domain covalently linked to a candidate molecule;

(e) a means for inserting into the first vector or the second vector a DNA encoding the known receptor domain in such a manner that the known receptor domain and an expression product of the first or second vector are expressed as a fusion protein;

(f) a means for inserting into the first vector or the second vector a DNA encoding the known target receptor in such a manner that the known target receptor and an expression product of the first or second vector are expressed as a fusion protein; and (g) a means for transfecting the host cell with the first vector, and the second vector, wherein binding of the dimeric small molecule to the known target receptor results in a measurably greater expression of the reporter gene then in the absence of such binding.

The elements of this kit are as defined previously.

This invention further provides a kit for identifying an unknown target receptor to which a molecule is capable of binding in a bacterial cell, comprising (a) a host bacterial cell containing a reporter gene that is expressed only when bound to a DNA-binding domain and when in the proximity of a transcription activation domain;

(b) a first vector containing a promoter that functions in the host bacterial cell and a DNA encoding a DNA-binding domain;

(c) a second vector containing a promoter that functions in the host bacterial cell and a DNA encoding a transcription activation domain;

(d) a dimeric small molecule which comprises a moiety that binds a known receptor domain covalently linked to a moiety against which the unknown target is to be screened for binding;

(e) a means for inserting into the first vector or the second vector a DNA encoding the known receptor domain in such a manner that the known receptor domain and an expression product of the first or second vector are expressed as a fusion protein;

(f) a means for inserting into the first vector or the second vector a DNA encoding the unknown target receptor in such a manner that the unknown target receptor and an expression product of the first or second vector are expressed as a fusion protein; and (g) a means for transfecting the host cell with the first vector, and the second vector, wherein binding of the dimeric small molecule to the unknown target receptor results in a measurably greater expression of the reporter gene then in the absence of such binding.

The elements of this kit are as defined previously.

This invention yet further provides a process for screening a chemical library for a molecule that binds a known target receptor, comprising providing a chemical library, providing a bacterial cell that expresses the known target receptor as a part of a fusion protein, and identifying the molecule that binds the known target receptor in the bacterial cell by the method described above. As a result, this invention also provides a molecule identified by the method, wherein the molecule was not previously known to bind the known target receptor.

This invention yet further provides a process for screening a cDNA library for a nucleic acid that encodes a receptor to which a known molecule binds, comprising providing a cDNA library, providing a dimeric molecule having two ligands, of which one ligand is the known molecule, and identifying the nucleic acid that encodes the receptor to which the known molecule binds by the method described above. As a result, this invention also provides an isolated nucleic acid identified by the process, wherein the isolated nucleic acid was not previously known to encode a receptor to which the known molecule binds. The isolated nucleic acid can encode an enzyme or a portion thereof.

This invention also provides a transgenic bacterial cell comprising (a) a dimeric small molecule which comprises a methotrexate moiety covalently linked to a moiety capable of binding a receptor domain;

(b) nucleotide sequences which upon transcription encode
    i) a first fusion protein comprising a DHFR domain and a first fragment of an enzyme, and
    ii) a second fusion protein comprising the receptor domain and a second fragment of the enzyme, wherein activity of the enzyme is conditioned on the proximity of the first fragment of the enzyme to the second fragment of the enzyme.

The elements of the cell are as described above.

This invention also provides a method for identifying a molecule that binds a known target receptor in a bacterial cell from a pool of candidate molecules, comprising:

(a) forming a dimeric molecule by covalently bonding each molecule in the pool of candidate molecules to a methotrexate moiety;

(b) introducing the dimeric molecule into a bacterial cell culture comprising bacterial cells that express
    a first fusion protein which comprises the known target receptor domain against which the candidate molecule is screened, and a first fragment of an enzyme, and
    a second fusion protein which comprises a DHFR receptor domain and a second fragment of the enzyme;

(c) permitting the dimeric molecule to bind to the first fusion protein and to the second fusion protein, bringing the first fragment and the second fragment of the enzyme in to proximity so as to reconstitute the activity of the enzyme;

(d) selecting the bacterial cell that exhibits the activity of the enzyme; and (e) identifying the small molecule that binds the known target receptor.

The elements of this method are as defined previously.

This invention also provides a method for identifying an unknown target receptor to which a known molecule is capable of binding in a bacterial cell, comprising:

(a) providing a dimeric molecule having a first ligand which has a specificity for the unknown target receptor covalently bonded to a methotrexate moiety;

(b) introducing the dimeric molecule into a bacterial cell which expresses
    a first fusion protein which comprises the unknown target receptor domain, and a first fragment of an enzyme, and
    a second fusion protein which comprises a DHFR receptor domain and a second fragment of the enzyme;

(c) permitting the dimeric molecule to bind to the first fusion protein and to the second fusion protein, bringing the first fragment and the second fragment of the enzyme in to proximity so as to reconstitute the activity of the enzyme;

(d) selecting the bacterial cell that exhibits the activity of the enzyme; and (e) identifying the unknown target receptor.

The elements of this method are as defined previously.

Each of the ligand halves of the dimeric small molecule may be derived from a compound selected from the group consisting of steroids, hormones, nuclear receptor ligands, cofactors, antibiotics, sugars, enzyme inhibitors, and drugs.

Each of the ligand halves of the dimeric small molecule may also represent a compound selected from the group consisting of 3,5,3'-triiodothyronine, trans-retinoic acid, biotin, coumermycin, tetracycline, lactose, methotrexate, FK506, and FK506 analogs.

In the described methods, the screening is performed by Fluorescence Associated Cell Sorting (FACS), or gene transcription markers selected from the group consisting of Green Fluorescence Protein, lacZ-β-galagctosidases, luciferase, antibiotic resistant b-lactamases, and yeast markers.

The known moiety that binds a known receptor domain can be a Methotrexate moiety or an analog thereof. The known receptor domain can be dihydrofolate reductase ("DHFR") generally, or the $E.\ coli$ DHFR ("eDHFR"). Alternatively, the pairing can be FK506/FKBP12, AP series of synthetic FK506 analogs/FKBPs, tetracycline/tetracycline repressor, cephem/penicillin binding protein. The penicillin binding domain can be from $Streptomyces$ R61.

Each of the methods is readily adapted to identify which substrate from a pool of candidate substrates is selected in a cell by a known enzyme for a bond forming reaction between the substrate and a known amino acid.

The described methods, cell and kit may also be adapted to identify new protein targets for pharmaceuticals.

The described methods, cell and kit may also be adapted for determining the function of a protein, further including screening with a natural cofactor being part of the CID.

The described methods, cell and kit may also be adapted for determining the function of a protein, further including screening with a natural substrate being part of the CID.

The described methods, cell and kit may also be adapted for screening a compound for the ability to inhibit a ligand-receptor interaction.

The foregoing embodiments of the subject invention may be accomplished according to the guidance which follows. Certain o f the foregoing embodiments are exemplified. Sufficient guidance is provided for a skilled artisan to arrive at all of the embodiments of the subject invention.

Preparation and Design of Ligand Halves of the Dimeric Small Molecule

A ligand half should bind its receptor with high affinity ($\leq 100$ nM), cross cell membranes yet be inert to modification or degradation, be available in reasonable quantities, and present a convenient side-chain for routine chemical derivatization that does not disrupt receptor binding.

A commercial source of traditional, non-covalent dimeric molecules for use in a chemically induced dimerization system is ARIAD (www.ariad.com), who call their CID "ARGENT TECHNOLOGY." The compounds described herein as well as other commercial compounds can be derivatized for use in the bacterial three-hybrid system.

For example, methotrexate ("Mtx") is an attractive ligand half (also referred to as "chemical handle"). Mtx inhibition of dihydrofolate reductase (DHFR) is one of the textbook examples of high-affinity ligand binding. The interaction between Mtx and DHFR is extremely well characterized in the literature both biochemically and structurally. DHFR is a monomeric protein and binds Mtx with picomolar affinity (11). Even though Mtx inhibits DHFR with such high affinity, $E.\ coli$ grows in the presence of Mtx when supplemented with appropriate nutrients (12). The ability of Mtx to serve both as an antibacterial and an anticancer agent is clear evidence that Mtx has excellent pharmacokinetic properties.

Mtx is known to be imported into cells via a specific folate transporter protein. Mtx is commercially available and can be synthesized readily from simple precursors. Mtx can be modified selectively at its g-carboxylate without disrupting its interaction with DHFR (11, 13). Mtx is commercially available and can be modified selectively at its γ-carboxylate without disrupting dihydrofolate reductase (DHFR) binding (11, 13). Even though Mtx inhibits DHFR with pM affinity (12), both $E.\ coli$ and $S.\ cerevisiae$ grow in the presence of Mtx when supplemented with appropriate nutrients (13).

However, not all ligand halves, also referred to as chemical handles, can be readily used in a given organism without the need to modify the organism. For instance, dexamethasone requires several heat-shock proteins ("HSPs"), in order to be bound by the glucocorticoid receptor ("GR"). The required HSPs occur in yeast and other eukaryotes; however, since bacteria lack these HSPs and thus GR fails to bind Dex, Dex based small molecules would not readily work in a bacterial three-hybrid system. Similarly, using Mtx in bacteria requires special adaptation of the bacterial cell as Mtx can actually act as an antibiotic, as discussed in more detail in the examples. Mtx is exported from the bacterial cell by the TolC-dependent multi-drug efflux pump (32). Knocking out the tolC gene allows Mtx-based molecules to not only enter the bacterial cell but remain there as well. Furthermore, knocking out thyA removed the toxic effects associated with Mtx by preventing the bio-accumulation of the toxic dihydrofolate substrate of DHFR (32). However, as discussed in detail in the example, knocking out the thyA, e.g through a mutation, is not necessary at the concentrations of Mtx that is used in the described bacterial three-hybrid system. While to use Mtx in the exemplified system, one must only knock out the tolC gene/protein in order to assure that Mtx-based molecules remain in the cell, it is clearly possible to also knock out thyA for higher concentrations of Mtx.

Other ligand halves may be, for example, steroids; enzyme inhibitors, such as Methotrexate used herein; drugs, such as FK506; hormones, such as the thyroid hormone 3,5,3'-triiodothyronine; ligands for nuclear receptors may be retinoic acids; general cofactors, such as Biotin; and antibiotics, such as Coumermycin (which can be used to induce protein dimerization according to Perlmutter et al., Nature 383, 178 (1996)).

One, or both, of the ligand halves may also be a moiety that is a substrate for an enzyme, i.e. a moiety that would not on its own bind to a protein, but would require an enzyme to assist bonding to a protein. In this way, the system can be made dependent on an enzyme, and would only operate when an enzyme is present. Such an enzyme would form a covalent bond between the small non-peptide molecule and a protein. This would provide flexibility in the system by allowing for one of the non-covalent interactions to be replaced by a covalent interaction.

Similarly, one, or both, of the ligand halves may be a moiety that spontaneously seeks out and forms a covalent bond with a receptor. An example of this is the interaction between Fluorouracil and Thymidylate Synthase, and another between Cephen and the Penicillin Binding Protein. This would also provide flexibility in the system by allowing for one of the non-covalent interactions to be replaced by a covalent interaction.

Linkage of the Ligand Halves in the Dimeric Small Molecule

While the ligand halves can be simply linked by a covalent bond between the two of them, more elaborate linkages may also be used depending on the screen to be performed. The linkage may be formed by any of the methods known in the art (14, 15). Descriptions of linkage chemistries are also provided by WO 94/18317, WO 95/02684, WO 96/13613, W096/06097, and WO 01/53355, these references being incorporated herein by reference. The linkers are all commercially available or can be prepared in a single step. The linkers vary in hydrophobicity, length, and flexibility.

The linker may be designed to respond to enzymatic activity. For example, a linker can contain a glycosidase bond, which may be cleaved by a glycosidase enzyme and formed by a Glycosyltransferase enzyme; or an amide bond, which may be cleaved by a protease and formed by peptidase or transpeptidase; or an aldol product bond, which is cleaved by a retro-aldolase and formed by aldolase; or an ester bond; or a phosphodiester bond. Such bonds can be used in bacterial based screens similarly to their use in yeast based screens, which are described in WO 01/53355.

The enzymes that act on such linkers may be known enzymes or novel proteins which are being screened for specific enzymatic activity. Novel enzymes can be evolved using combinatorial techniques.

Once a desired substrate is selected and formed into the dimeric small molecule, a large number of enzymes and derivatives of enzymes can be screened. A variety of enzymes and enzymes classes are listed on the World Wide Web beginning at prowl.rockefeller.edu/enzymes/enzymes.htm. All enzymes are given an Enzyme Commission (E.C.) number allowing it to be uniquely identified. E.C. numbers have four fields separated by periods, "a.b.c.d". The left-hand-most field represents the most broad classification for the enzyme. The next field represents a finer division of that broad category. The third field adds more detailed information and the fourth field defines the specific enzyme. Thus, in the "a" field the classifications are oxidoreductases, transferases, hydrolases, lyases, isomerases, and ligases. Each of these "a" classifications are then further separated into corresponding "b" classification, each of which in turn is separated into corresponding "c" classifications, which are then further separated into corresponding "d" classes.

Moreover, new enzymes are discovered and are intended to be included within the scope of this invention, which is itself designed to evolve or discover such new enzymes.

Design of the Protein Chimeras

The second important feature is the design of the protein chimeras. A number of chimeras are discussed in detail in WO 01/53355.

The described bacterial three-hybrid system is based on the RNA polymerase two-hybrid system reported by Dove and Hochschild in 1997 (16). A variety of methods for detecting protein-protein interactions in bacteria are now available. (8–10, 16–19). Generally, these methods are based either on enzyme complementation or transcriptional activation or repression assays. While the enzyme complementation assays are essentially the same as those used in eukaryotes, entirely new transcription-based assays had to be developed for bacteria because the components of the transcription machinery are poorly conserved between eukaryotes and prokaryotes. The choice to adapt the RNA polymerase assay developed by Dove and Hochschild was because transcriptional activation in this assay results in a large increase in reporter gene transcription and because reconstitution of transcriptional activation was expected to be largely conformation independent. Based on their studies of the mechanism of transcriptional activation by λ-repressor (λcI) (20), Dove and Hochschild developed an in vivo assay for protein-protein interactions based on dimerization of λcI and the N-terminal domain of the α-subunit of RNA polymerase (αNTD). Specifically, they designed a reporter construct consisting of a λcI operator upstream of the TATA box for the lacZ gene, which encodes β-galactosidase. They then prepared plasmids encoding a Gal4-λcI fusion protein and a Gal11$^P$-αNTD fusion protein. Gal4 and Gal11$^P$ are two proteins known to interact with high affinity and so provided a well-established test case. Finally, the interaction between Gal4-λcI and Gal11$^P$-αNTD was shown to activate transcription of the lacZ reporter gene (21). This original Gal4-Gal11$^P$ two-hybrid system is used as a small-molecule independent positive control in the example provided below.

Design of Reporter Genes

A reporter gene assay measures the activity of a gene's promoter. It takes advantage of molecular biology techniques, which allow one to put heterologous genes under the control of a bacterial cell. Activation of the promoter induces the reporter gene as well as or instead of the endogenous gene. By design, the reporter gene codes for a protein that can easily be detected and measured. Commonly it is an enzyme that converts a commercially available substrate into a product. This conversion is conveniently followed by either chromatography or direct optical measurement and allows for the quantification of the amount of enzyme produced.

Reporter genes are commercially available on a variety of plasmids for the study of gene regulation in a large variety of organisms (22). Promoters of interest can be inserted into multiple cloning sites provided for this purpose in front of the reporter gene on the plasmid (23, 24). Standard techniques are used to introduce these genes into a cell type or whole organism (e.g., as described in Sambrook, J., Fritsch, E. F. and Maniatis, T. Expression of cloned genes in cultured mammalian cells. In: *Molecular Cloning*, edited by Nolan, C. New York: Cold Spring Harbor Laboratory Press, 1989). Resistance markers provided on the plasmid can then be used to select for successfully transfected cells.

Ease of use and the large signal amplification make this technique increasingly popular in the study of gene regulation. Every step in the cascade DNA→RNA→Enzyme→Product→Signal amplifies the next one in the sequence. The further down in the cascade one measures, the more signal one obtains.

In an ideal reporter gene assay, the reporter gene under the control of the promoter of interest is transfected into cells, either transiently or stably. Receptor activation leads to a change in enzyme levels via transcriptional and translational events. The amount of enzyme present can be measured via its enzymatic action on a substrate.

Reconstitution of Enzyme Activity

In lieu of the protein chimeras or reporter genes as described above, the reassembly of an enzyme, and thus its activity, can be used as a reporter system. Complementation between enzyme fragments has been observed in numerous cases since the pioneering discovery of intracistronic complementation by Ullmann and colleagues in 1967. The so-called α-complementation between two truncated β-galactosidase polypeptides became a classical tool in molecular biology for cloning techniques and has recently found new interest in cell biology as a sensitive marker of eukaryotic cell fusions and a reporter.

Potentially, a large number of enzymes might be split into two complementary fragments that could reassociate to reconstitute the native enzymatic activity. Functional complementation between two enzyme fragments can be exploited to design a three-hybrid system provided that: (i) the cognate enzymatic activity is easily detected or selected for in vivo; (ii) the two fragments do not reassociate spontaneously when expressed as separate entities (as do, for example, the classical LacZ-α and α-acceptor); (iii) when fused to interacting polypeptides, the two fragments reassociate in an enzymatically active complex. A variety of enzyme reassembly systems have been described (37). For example, a protein complementation assay based on engineered fragments of mouse dihydrofolate reductase (mDHFR) has been described (38). Subsequently, the same group used the mDHFR complementation assay to select pairs of leucine zippers that selectively heterodimerize.

One advantage of an enzyme reconstitution assay is that it can work in cells which do not endogenously express the enzyme, thus providing an efficient reporter system.

This invention will be better understood from the Experimental Details which follow. However, one skilled in the art will readily appreciate that the specific methods and results discussed are merely illustrative of the invention as described more fully in the claims which follow thereafter.

Experimental Details

Part I—Preparation of Dimeric Small Molecule Ligand

In order to convert the Dove and Hoschild two-hybrid assay into a three-hybrid system, it was initially important to design a dimeric ligand that could bridge λcI and αNTD via the ligand's receptors. For the bridging small molecule, a heterodimer of methotrexate (Mtx) and a synthetic analog of FK506 (SLF) was prepared. This heterodimer is referred to in this description Mtx-SLF. Mtx-SLF was used to dimerize a λcI-FK506 binding protein 12 (λcI-FKBP12) protein chimera and an αNTD-dihydrofolate reductase (αNTD-DHFR) protein chimera as shown in FIG. 1. Methotrexate (Mtx) inhibits dihydrofolate reductase (DHFR) with a low picomolar $K_f$, and the interaction between the two has been extensively studied (11, 25). In addition, our laboratory recently showed Mtx could be used successfully in a yeast three-hybrid system (7, 26). For the other half of the bridging small molecule, we used SLF, available from Ariad Pharmaceuticals as an FK506 analog. SLF has nanomolar affinity for FKBP12, and the interaction between the two has been fully characterized (27,28). In addition, SLF homodimers have been used previously in several mammalian three-hybrid systems (29).

Figure 2:
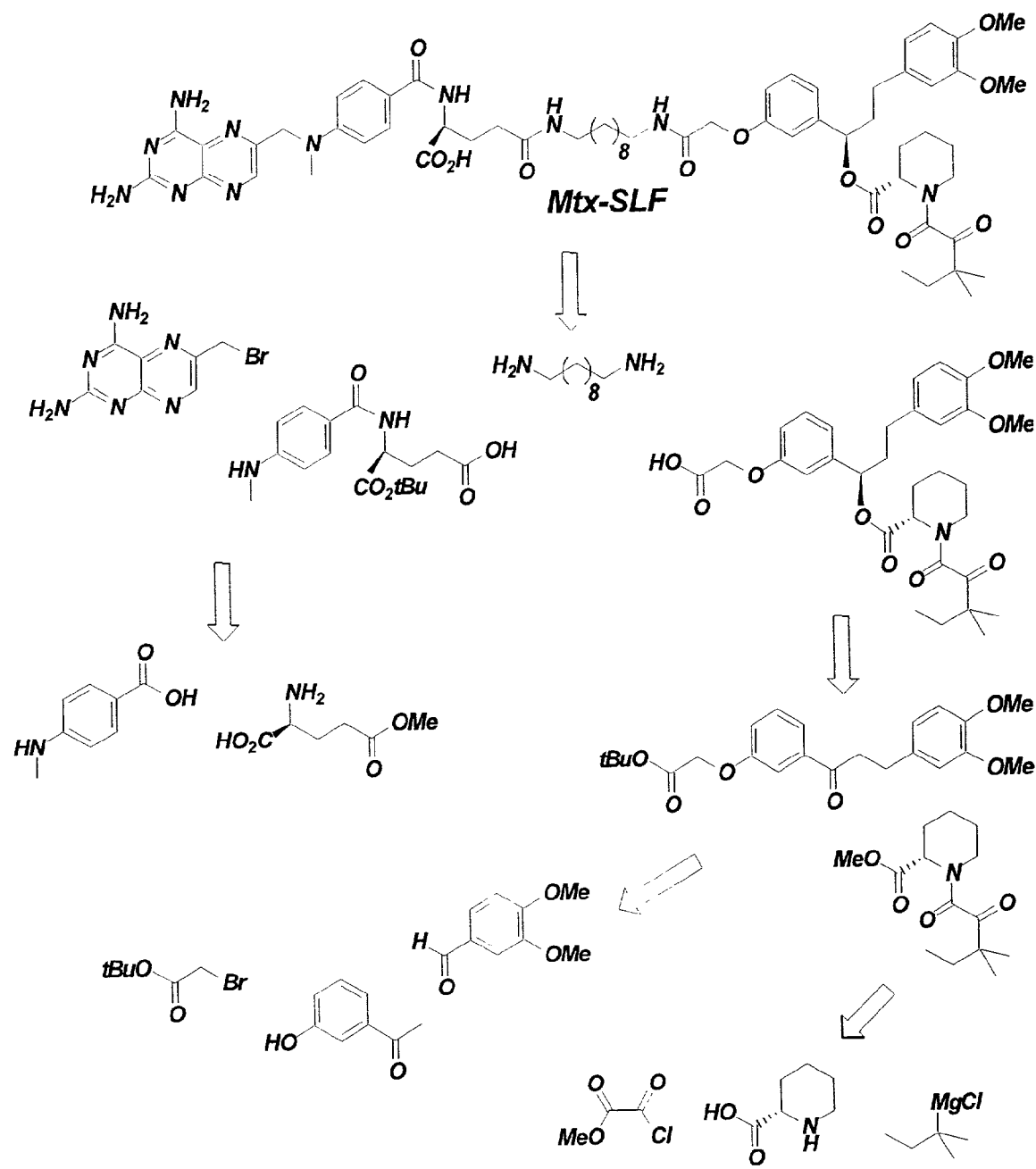
FIG. 2. Retrosynthetic analysis of Mtx-SLF.

The retrosynthetic analysis of Mtx-SLF is shown in FIG. 2. The synthesis is based on previous syntheses of Mtx and SLF derivatives and was designed to allow Mtx, SLF, or the linker between them to be varied readily. The Mtx portion of the molecule begins as the γ-methyl ester of L-glutamic acid and is based on previous syntheses of Mtx (7,26,30). γ-Methyl L-glutamic acid is inexpensive, and the α-carboxylate can be selectively protected as the tert-butyl ester by transiently protonating the α-amino group (31). The diprotected amino acid is then coupled to 4-(methylamino)benzoic acid using standard peptide coupling reagents. Finally, the γ-methyl ester is saponified to yield the free acid for further reactions. SLF acid was synthesized as described previously from L-pipecolinic acid in 59% yield for 6 steps (6,27). The Mtx and SLF portions were then coupled to 1,10-diaminodecane in a three-component peptide coupling reaction. 2,4-Diamino-6-bromomethyl-pteridine is added after this coupling reaction in order to simplify purification of the synthetic intermediates. Finally, acid cleavage of the tert-butyl ester yielded Mtx-SLF. Thus, the Mtx-SLF heterodimer was prepared from two components in 5% overall yield for the 6 steps from the γ-methyl ester of L-glutamic acid or 6% overall yield in 9 steps from the L-pipecolinic acid precursor of SLF.

The synthetic chemistry performed for the preparation of the Mtx-SLF is described below.

Synthetic Chemistry

General Methods. Reagents were obtained from commercial suppliers and were used without further purification. All reagents for chemical synthesis were purchased from Aldrich. Anhydrous N,N-dimethylformamide and anhydrous methylene chloride were from Sure Seal™ bottles purchased from Aldrich. Methotrexate was a generous gift from the National Cancer Institute. Nuclear magnetic resonance (NMR) spectra were recorded on a Bruker 500 (500 MHz), a Bruker 400 (400 MHz) or a Bruker 300 (300 MHz) Fourier Transform (FT) NMR spectrometer at the Columbia University Chemistry Department NMR Facility. Spectra were determined in methanol-$d_4$ at 300 K with the proton or carbon (3.30δ; 49.0δ) as the reference or in chloroform-d at 300K with proton (7.26δ) as the reference. $^1$H NMR spectra are tabulated in the following order: chemical shift calculated with reference to solvent standards based on tetramethylsilane, multiplicity (s, singlet; d, doublet; t, triplet; m, multiplet; br, broad), coupling constants) in Hertz, and number of protons. $^{13}$C NMR spectra were determined on the Bruker 300 MHz instrument and are proton decoupled. Mass spectra (MS) were recorded at the Columbia University Department of Chemistry mass spectral laboratory. Fast Atom Bombardment (FAB) high resolution mass spectra (HRMS) were recorded on a JMS-HX110A mass spectrometer. Low resolution electron spray ionization mass spectra (LRMS) were recorded on a JMS-LC Mate mass spectrometer. Analytical thin layer chromatography (TLC) was performed on silica gel (Whatman LHPKF Silica Gel 60 Å) and visualized by UV light (254 nm) or stained by ninhydrin. All column chromatography was flash chromatography carried out on silica gel (EM Science Silica Gel 60), and all eluants used are reported in volume:volume ratios. All moisture-sensitive reactions were performed under a positive pressure of nitrogen in flame- or oven-dried glassware. Organic extracts were dried over anhydrous sodium sulfate. Organic solvents were removed in vacuo with a rotary evaporator equipped with a vacuum pump (ca. 1 torr). Products were then left under vacuum (ca. 0.1 torr) overnight before analysis was performed.

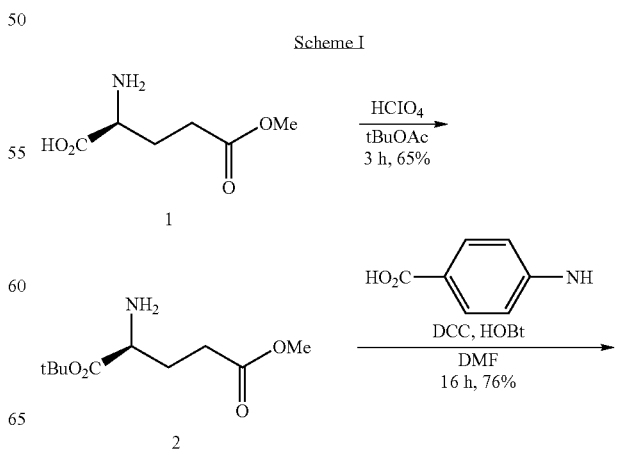

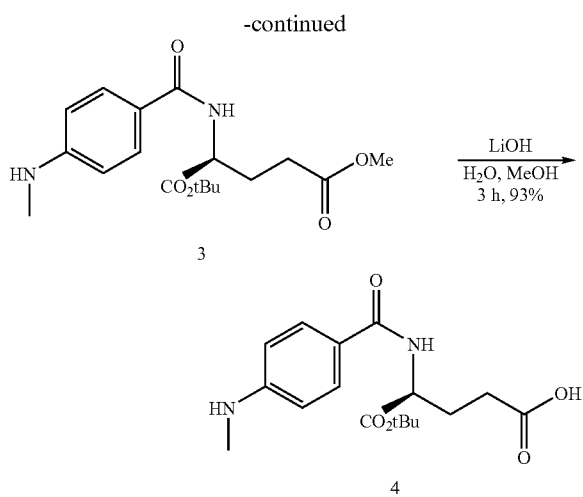

Synthesis of 2. (31) The γ-methyl ester of L-glutamic acid (1) (5.02 g, 31.0 mmol) was added to a solution of 70% aqueous (aq.) perchloric acid (3.0 mL) in tert-butyl acetate (200 mL). The resulting solution was stirred at room temperature (rt) for 3 h during which time the acid dissolves completely. The reaction was then judged complete by thin layer chromatography (TLC) using 10:1 methylene chloride ($CH_2Cl_2$):methanol (MeOH). The reaction mixture was extracted with 0.5 N aq. HCl (4×, 400 mL). The pH of the combined aqueous layers was adjusted to 8 using saturated aq. sodium carbonate. The aqueous solution was then extracted with ethyl acetate (EtOAc) (4×, 500 mL). The organic extracts were combined, washed with brine (2×, 300 mL), and dried over anhydrous sodium sulfate. Removing the solvent in vacuo gave 2 as a clear oil in 65% yield: $R_f$=0.45 in 10:1 $CH_2Cl_2$:MeOH; $^1$H NMR (400 MHz, $CD_3OD$) δ 3.66 (s, 3), 3.33 (t, J=6.5 Hz, 1), 2.41 (m, 2), 1.95 (m, 1), 1.86 (m, 1); LRMS, m/z 218.2 ($MH^+$), 219.2 ($MH_2^+$).

Synthesis of 3. (7,30) Compound 2 (2.19 g, 10.0 mmol), 1,3-dicyclohexylcarbodiimide (DCC, 3.09 g, 15.0 mmol), 1-hydroxylbenzotriazole hydrate (HOBt, 2.43 g, 18.0 mmol), and N-methyl-para-benzoic acid (1.59 g, 10.5 mmol) were dissolved in anhydrous dimethyl formamide (DMF, 22 mL) under a nitrogen atmosphere. Diisopropylethylamine (DIEA, 0.1 mL, 0.5 mmol) was added to the solution, and the reaction mixture was stirred overnight (ON) at rt. After 16 hr, a 1:2:1 water:saturated aq. sodium bicarbonate:brine solution (500 mL) was added to the reaction giving a yellow suspension. This solution was then extracted with EtOAc (4×, 300 mL). The fractions were combined, washed with brine (2×, 200 mL) and dried over anhydrous sodium sulfate. The organic solvent was then removed in vacuo. The product is purified by silica gel column chromatography (2:1 to 1:1 hexanes:EtOAc) in 76% yield: $R_f$=0.25 in 1:1 hexanes:EtOAc; $^1$H NMR (500 MHz, $CD_3OD$) δ 7.66 (d, J=7.0 Hz, 2), 6.58 (d, J=7.0 Hz, 2), 4.59 (dd, J=9.5, 5.0 Hz, 1), 3.65 (s, 3), 2.79 (s, 3), 2.47 (t, J=7.5 Hz, 2), 2.23 (m, 1), 2.05 (m, 1), 1.46 (s, 9); $^{13}$C NMR (300 MHz, $CD_3OD$) δ 175.1, 173.0, 170.6, 154.6, 130.2, 121.5, 111.9, 82.9, 54.3, 52.3, 31.4, 30.0, 28.3, 27.6; LRMS, m/z 351.2 ($MH^+$); HRMS, m/z 351.1930 ($MH^+$), calculated 351.1920.

Synthesis of 4. Compound 3 (500 mg, 1.43 mmol) was dissolved in methanol (20 mL). Lithium hydroxide monohydrate (120 mg, 2.86 mmol) was dissolved in water. Both solutions were chilled in a 0° C. ice bath. The aqueous solution was added to the methanol solution all at once. The resulting solution was stirred at 0° C. for 10 minutes and then allowed to warm to rt and stirred for an additional 80 minutes. Solvent is removed in vacuo until only a yellow gel remained with a volume about 1 mL. Water (20 mL) was added to the remaining reaction mixture. The solution was acidified to pH=2 with 1 N aq. HCl (9 mL) and was immediately extracted with EtOAc (5×, 25 mL). The organic extracts were combined, washed with brine (2×, 20 mL), and dried over anhydrous sodium sulfate. The solvent was removed in vacuo to yield product 4 in 93% yield: $R_f$=0.05 in 1:1 EtOAc:hexanes and 0.45 in 5:1 $CH_2Cl_2$:MeOH; $^1$H NMR (400 MHz, $CD_3OD$) δ 7.64 (d, J=7.0 Hz, 2), 6.56 (d, J=7.0 Hz, 2), 4.46 (dd, J=9.0, 5.0 Hz, 1), 2.80 (s, 3), 2.44 (t, J=7.5 Hz, 2), 2.23 (m, 1), 2.05 (m, 1), 1.47 (s, 9); $^{13}$C NMR (300 MHz, $CD_3OD$) δ 178.4, 174.8, 172.3, 156.2, 130.7, 123.2, 113.6, 84.6, 57.0, 33.2, 31.8, 30.5, 29.1; LRMS, m/z 337.3 ($MH^+$); HRMS, m/z 337.1751 ($MH^+$), calculated 337.1763.

Scheme II

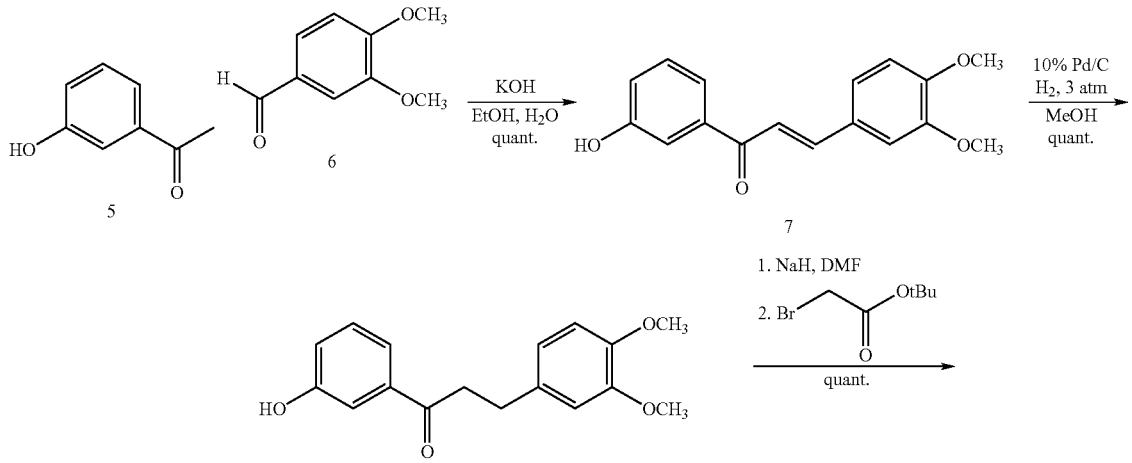

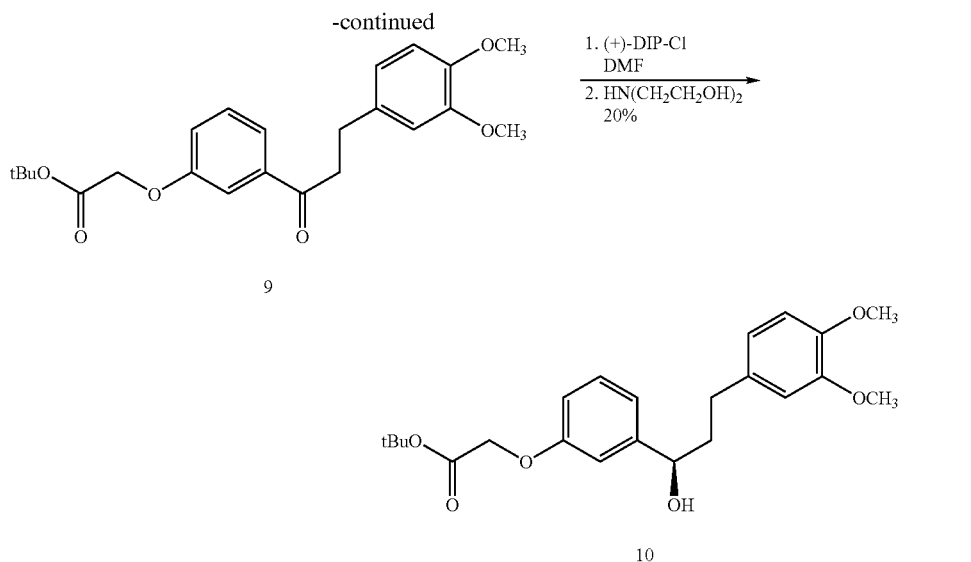

Synthesis of 7. (27) Synthesized as reported in quantitative yield to give 7 as a yellow solid: $R_f$=0.40 in 1:1 EtOAc:hexanes; $^1$H NMR (300 MHz, CDCl$_3$) δ 9.86 (s, 1), 7.61–7.55 (m, 2), 7.40–7.34 (m, 2), 7.32 (d, J=4.5 Hz, 1), 7.25–7.10 (m, 2), 6.91–6.85 (m, 2), 3.95 (s, 3), 3.93 (s, 3); LRMS, m/z 284.9 (MH$^+$).

Synthesis of 8. (27) Synthesized as reported in near quantitative yield based on mass as a white crystalline solid (NMR revealed a small amount of non-hydrogenated starting material remains and is carried through to the next step. NMR integration is used to determine relative quantities of the two materials.): $R_f$=0.50 in 1:1 EtOAc:hexanes; $^1$H NMR (300 MHz, CDCl$_3$); δ 7.55–7.48 (m, 2), 7.35 (t, J=8.0 Hz, 1), 7.25 (t, J=8.5 Hz, 1), 7.10 (br d, J=8.0 Hz, 1), 6.91–6.73 (m, 3), 3.90 (s, 3), 3.88 (s, 3), 3.24 (t, J=7.5 Hz, 2), 2.99 (t, J=8.0 Hz, 2); LRMS, m/z 287.0 (MH$^+$).

Synthesis of 9. (27) Synthesized as reported to give 9 as a clear oil in quantitative yield by mass: $R_f$=0.60 in 1:1 EtOAc:hexanes; $^1$H NMR (300 MHz, CDCl$_3$) δ 7.59 (br d, 8.0 Hz, 1), 7.49 (m, 1), 7.37 (t, J=8.0 Hz, 1), 7.14 (dd, J=8.0, 2.5 Hz, 1), 6.85–6.72 (m, 3), 4.60 (s, 2), 3.89 (s, 3), 3.86 (s, 3), 3.27 (t, J=7.1 Hz, 2), 3.04 (t, J=7.5 Hz, 2), 1.50 (s, 9).

Synthesis of 10. (27) Synthesized as reported to yield product 10 in 20% yield fully purified. However, a 75% yield of unreacted starting material was also recovered. $R_f$=0.40 in 5:1 CH$_2$Cl$_2$:MeOH and 0.40 in 1:1 EtOAc:hexanes; $^1$H NMR (500 MHz, CD$_3$OD) δ 7.28 (t, J=8.0 Hz, 1), 6.93 (d, J=7.5 Hz, 1), 6.89 (s, 1), 6.82 (d, J=8.0 Hz, 1), 6.80–6.74 (m, 2), 6.70 (d, J=8.0 Hz, 1), 4.60–4.53 (m, 3), 3.80 (s, 3), 3.78 (s, 3), 2.65–2.51 (m, 2), 2.04–1.89 (m, 2), 1.47 (s, 9); LRMS, m/z 403.3 (MH$^+$).

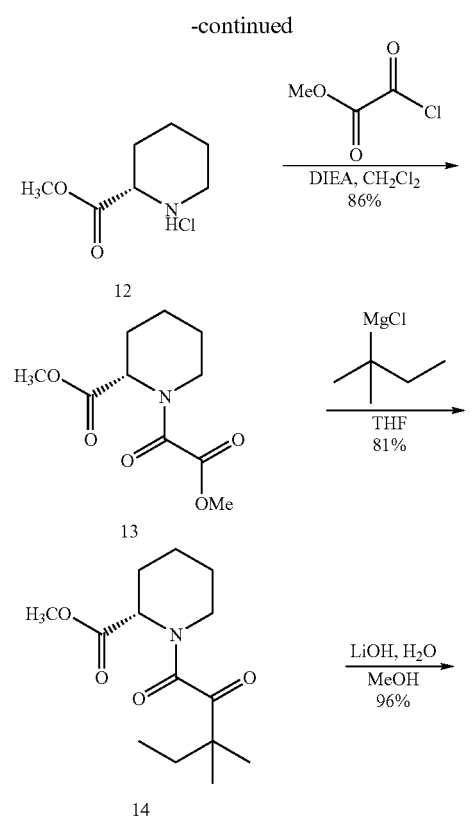

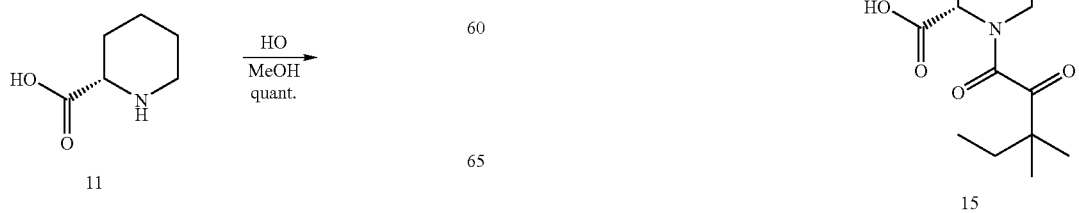

Synthesis of 12. (28) Synthesized as reported to give 12 as a white crystalline solid in quantitative yield based on NMR integration: $^1$H NMR (400 MHz, CD$_3$OD) δ 4.03 (br d, J=9.5 Hz, 1), 3.83 (s, 3), 3.41 (br d, J=12.0 Hz, 1), 3.04 (br t, J=11.0 Hz, 1), 2.27 (br d, J=11.5 Hz, 1), 2.00–1.63 (m, 5).

Synthesis of 13. (28) Synthesized as reported to yield 13 as a clear oil in 86% yield: $R_f$=0.70 in 1:1 EtOAc:hexanes and 0.25 in 1:4 EtOAc:hexanes; $^1$H NMR (500 MHz, CD$_3$OD) δ 5.15 (br d, J=5.0 Hz, 0.7), 4.62 (br d, J=4.0 Hz, 0.3), 4.34 (br d, J=12.0 Hz, 0.3), 3.89 (s, 2.1), 3.84 (s, 0.9), 3.77 (s, 3), 3.57 (br d, J=14.0 Hz, 0.7), 3.35 (m, 0.7), 2.91 (br t, J=13.0 Hz, 0.3), 2.35–2.24 (m, 1), 1.83–1.65 (m, 3) 1.55–1.35 (m, 2) This product exists as a 2.5:1 mixture of the trans and cis conformations. Further analysis by COSY allows us to make the following assignments of the two peaks for each proton in the structure: 5.15 and 4.62, 4.34 and 3.57, 3.89 and 3.84, 3.35 and 2.91; LRMS, m/z 230.1 (MH$_1^+$).

Synthesis of 14. (28) Synthesized as reported to give 14 as a clear oil in 81% yield: $R_f$=0.85 in 1:1 EtOAc:hexanes and 0.50 in 1:4 EtOAc:hexanes; $^1$H NMR (500 MHz, CD$_3$OD) δ 5.16 (br d, J=5.5 Hz, 0.8), 4.38 (br d, J=11.5 Hz, 0.2), 4.24 (br d, J=5.0 Hz, 0.2), 3.75 (s, 3), 3.39 (br d, J=13.0 Hz, 0.8), 3.23 (td, J=13.0, 2.8 Hz, 0.8), 2.91 (br t, J=13.0 Hz, 0.2), 2.30 (br d, J=14.0 Hz, 0.8), 2.22 (br d, J=13.5, 0.2), 1.79–1.60 (m, 5) 1.55–1.35 (m, 2), 1.23–1.13 (m, 6), 0.86 (t, J=7.5 Hz, 3) This product exists as a 4:1 mixture of the trans and cis conformations. Further analysis by COSY allows us to make the following assignments of the two peaks for each proton in the structure: 5.16 and 4.24, 4.38 and 3.39, 3.23 and 2.91, 2.30 and 2.22; LRMS, m/z 270.2 (MH$^+$).

Synthesis of 15. (28) Synthesized as reported to give the product 15 as a white crystalline material in 96% yield: $R_f$=0.05 in 1:1 EtOAc:hexanes; $^1$H NMR (500 MHz, CDCl$_3$) δ 5.29 (br d, J=5.5 Hz, 0.8), 4.50 (br d, J=14.0 Hz, 0.2), 4.26 (br d, J=4.5 Hz, 0.2), 3.43 (br d, J=13.0 Hz, 0.8), 3.24 (td, J=12.5, 3.5 Hz, 0.8), 2.94 (br td, J=13.0, 3 Hz, 0.2), 2.34 (br d, J=12.0 Hz, 0.8), 2.24 (br d, J=13.5, 0.2), 1.79–1.60 (m, 5) 1.55–1.35 (m, 2), 1.23–1.13 (m, 6), 0.86 (t, J=7.5 Hz, 3) This product exists as a 4:1 mixture of the trans and cis conformations. Further analysis by COSY allows us to make the following assignments of the two peaks for each proton in the structure: 5.29 and 4.24, 4.50 and 3.43, 3.24 and 2.94, 2.34 and 2.24. Compounds 16, 17, 18, and Mtx-SLF all have this same 4:1 conformation pattern and appear nearly the same spectroscopically as compound 15 for these peaks. For simplicity's sake the 0.8 integration will be called 1 and the 0.2 peak will be disregarded in the characterization for the rest of these compounds.

Scheme IV

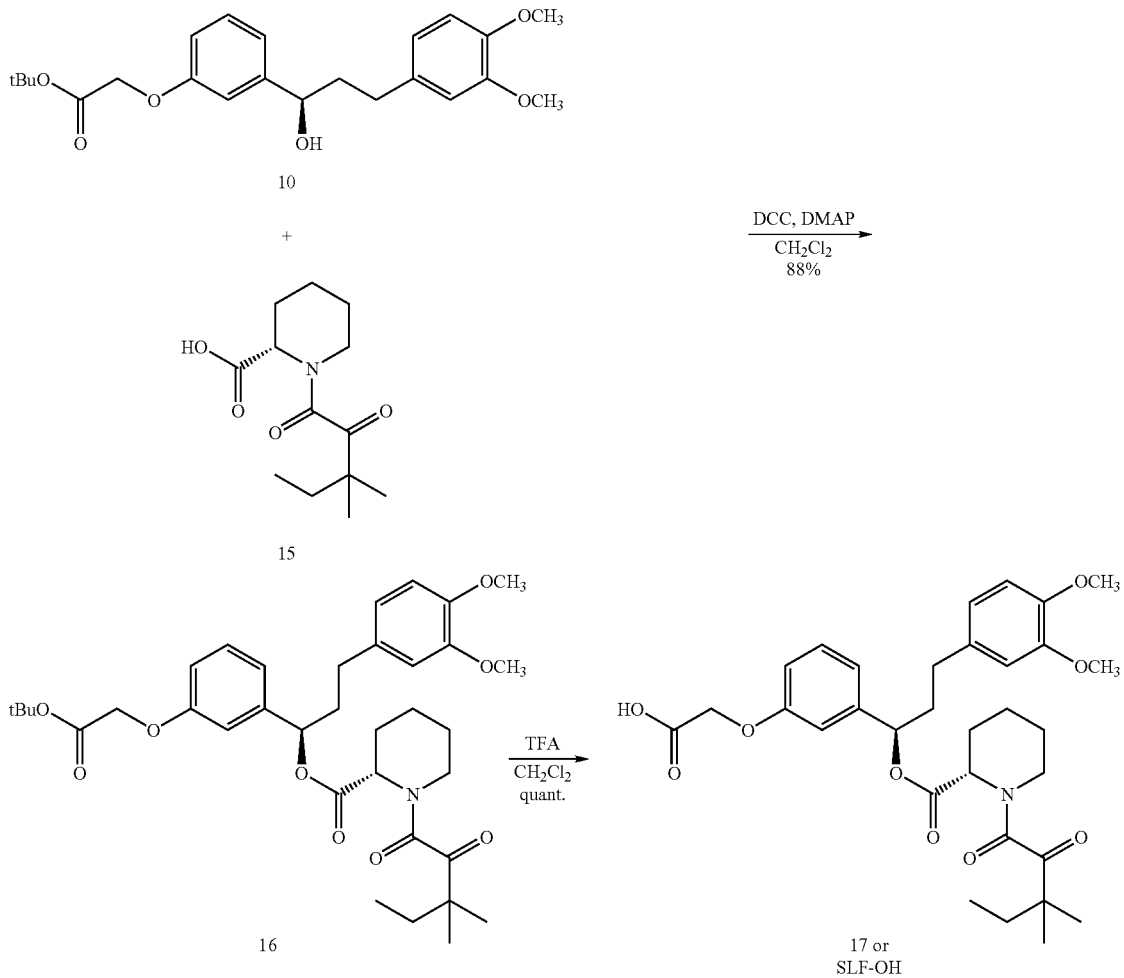

Synthesis of 16. (27) Synthesized as reported to give 16 as a colorless oil in 88% yield: $R_f$=0.15 in 4:1 hexanes:EtOAc and 0.65 in 1:1 EtOAc:hexanes; $^1$H NMR (500 MHz, CD$_3$OD) δ 7.28 (t, J=8.0 Hz, 1), 6.96 (m, 1), 6.89 (s, 1), 6.85 (m, 2), 6.78 (s, 1), 6.71 (d, J=8.0 Hz, 1), 5.73 (m, 1), 5.21 (br d, J=5.5 Hz, 1), 4.58 (s, 2), 3.80 (s, 3), 3.78 (s, 3), 3.38 (br d, J=14.5 Hz, 1), 3.17 (td, J=13.0, 3.0 Hz, 1), 2.65–2.52 (m, 2), 2.32 (br d, J=13.0 Hz, 1), 2.30–2.20 (m, 1), 2.05 (p, J=7.0 Hz, 1), 1.78–1.58 (m, 5), 1.46 (s, 9), 1.41–1.26 (m, 2), 1.23 (s, 3), 1.21 (s, 3), 0.86 (t, J=7.5 Hz, 3) (see note in Compound 15); LRMS, m/z 640.7 (MH$^+$).

Synthesis of 17. (27) Synthesized as reported to give 17 in quantitative yield. TLC analysis showed only one product and the acid was used without further purification: $R_f$=0.05 in 1:1 EtOAc:hexanes and 0.35 in 10:1 CH$_2$Cl$_2$:MeOH.

Synthesis of Mtx-SLF.(7,26,30) Compound 18 (40.0 mg, 38.0 μmol) and the hydrobromide salt of 2,4-diamino-6-bromomethyl pteridine (18 mg, 45 μmol) were dissolved in N,N'-dimethyl acetamide (2 mL). The reaction mixture was stirred in a 50° C. oil bath for 12 hours. The intermediate product ($R_f$=0.50 in 10:1 CH$_2$Cl$_2$:MeOH) was purified by silica gel column chromatography (30:1 to 10:1 CH$_2$Cl$_2$:MeOH). The crude product was dissolved in trifluoroacetic acid (3 mL) at 0° C. for 5 minutes and allowed to warm to rt and stirred at rt for 1 hour. Toluene (3×, 50 mL) was added to the reaction mixture, and all solvent was removed in vacuo. After removal of solvents, Mtx-SLF was purified by

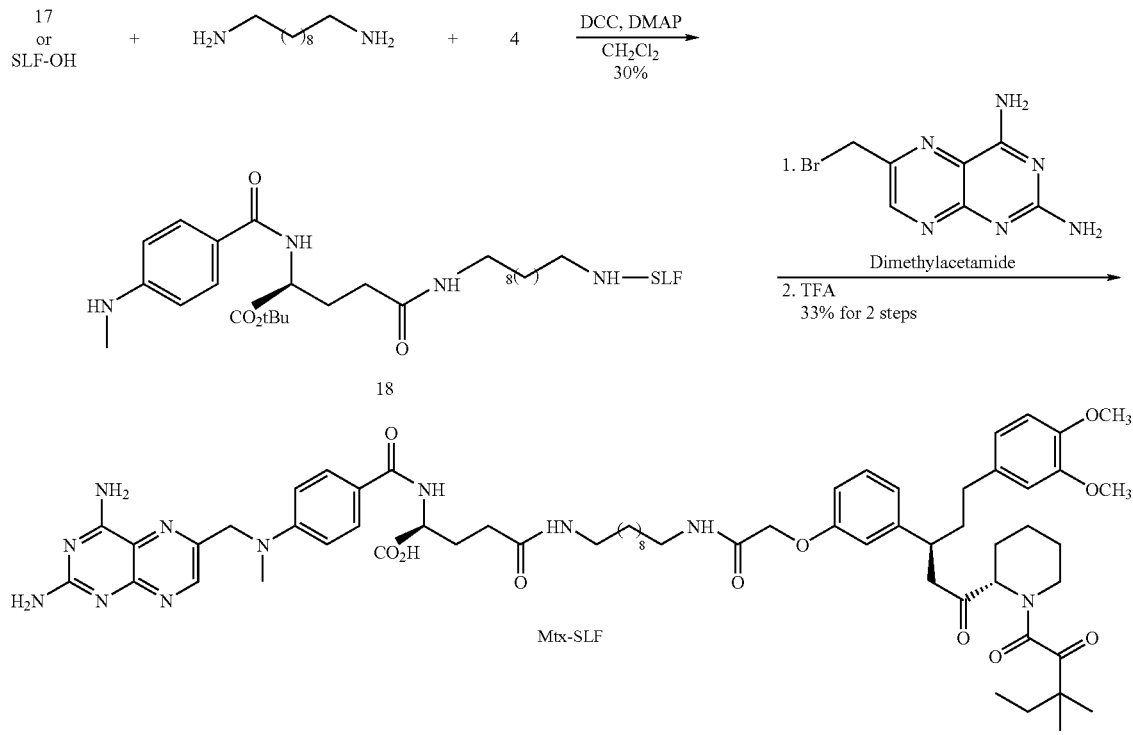

Scheme V

Synthesis of 18. Compound 4 (42.7 mg, 0.127 mmol), compound 17 (74.1 mg, 0.127 mmol), 1,10-diaminodecane (20.7 mg, 0.120 mmol), DCC (130 mg, 0.631 mmol), and DMAP (30.0 mg, 0.246 mmol) were dissolved in CH$_2$Cl$_2$ (3 mL) under a nitrogen atmosphere and stirred at rt overnight. After 16 hours, the solvent was removed in vacuo. The product was purified by silica gel column chromatography (1:4 EtOAc:hexanes to pure EtOAc) to give a white solid in 30% yield: $R_f$=0.65 in EtOAc and 0.60 in 10:1 CH$_2$Cl$_2$:MeOH; $^1$H NMR (500 MHz, CD$_3$OD) δ 7.64 (d, J=7.0 Hz, 2), 7.28 (td, J=8.0, 3.0 Hz, 1), 6.98 (m, 2), 6.91 (d, J=7.5 Hz, 1), 6.85 (d, J=8.0 Hz, 1), 6.76 (s, 1), 6.69 (d, J=8.0 Hz, 1), 6.56 (d, J=7.0 Hz, 2), 5.74 (m, 1), 5.21 (br d, J=5.0 Hz, 1), 4.51 (s, 2), 4.46 (m, 1), 3.80 (s, 3), 3.78 (s, 3), 3.38 (br d, J=12.5 Hz, 1), 3.23 (t, J=7.0 Hz, 2) 3.17 (td, J=13.0, 3.0 Hz, 1), 3.11 (t, J=7.0 Hz, 2), 2.80 (s, 3), 2.65–2.52 (m, 2), 2.37–2.30 (m, 3), 2.30–2.15 (m, 2), 2.10–2.00 (m, 2), 1.78–1.58 (m, 4), 1.48 (s, 9), 1.54–1.38 (m, 5), 1.38–1.28 (m, 2), 1.28–1.16 (m, 18), 0.86 (t, J=7.5 Hz, 3) (see note in Compound 15).

preparative thin layer silica gel chromatography (5:1 CH$_2$Cl$_2$:MeOH, 4×) to give a yellow solid in 33% yield (for two steps): $R_f$=0.15 in 3:1 CH$_2$Cl$_2$:MeOH; $^1$H NMR (500 MHz, CD$_3$OD) δ 8.55 (s, 1), 7.73 (d, J=8.0 Hz, 2), 7.28 (t, J=7.5 Hz, 1), 6.98 (m, 2), 6.91 (br d, J=7.5 Hz, 1), 6.85–6.79 (m, 3), 6.76 (s, 1), 6.69 (d, J=6.5 Hz, 1), 5.73 (m, 1), 5.21 (br s, 1), 4.75 (s, 2), 4.50 (s, 2), 4.46 (m, 1), 3.80 (s, 3), 3.78 (s, 3), 3.38 (br d, J=13.0 Hz, 1), 3.25–3.10 (m, 6), 3.05 (t, J=7.0 Hz, 2), 2.65–2.52 (m, 2), 2.37–2.15 (m, 5), 2.10–2.00 (m, 2), 1.78–1.58 (m, 4), 1.50–1.42 (m, 3), 1.38–1.32 (m, 3), 1.35–1.25 (m, 4), 1.25–1.16 (m, 15), 0.86 (t, J=7.5 Hz, 3) (see note in Compound 15).

Small molecule concentration calibration. The small molecules were dissolved in DMF to concentrations of 10 mM for Mtx and 12 mM for the Mtx-SLF molecule. The concentrations of Mtx and Mtx-SLF were determined by Beer's law using an extinction coefficient of ϵ=6700 cm$^{-1}$M$^{-1}$ (calculated from a known solution of Mtx in DMF) for Mtx-SLF. Solutions of compound 16 (SLF-OtBu) were prepared on a sufficient scale to mass 16 accurately. All small molecules were stored under a nitrogen atmosphere at −80° C. and allowed to come to rt before use.

Part II—Construction fo E. coli Strain.

The next step was the construction of the E. coli strain expressing the λcI-FKBP12 and (NTD-DHFR fusion proteins and containing the lacZ reporter construct. Plasmids encoding the λcI-FKBP12 and αNTD-DHFR chimeras were prepared from vectors pACλcI32 and pBRαLN using standard molecular biology techniques (8). The same synthetic lacZ reporter, placOR2-62, as initially reported by the Hochschild lab was used. The reporter placOR2-62 is maintained in one copy in the chromosome as a prophage and encodes the lacZ gene 62 bp downstream from the λcI operator (FIG. 1) (16). Based on previous results from Kopytek and Hu showing that tolC− and thyA− mutations improved the viability and tolerance of E. coli to Mtx-based molecules, we expected export as well as toxicity of Mtx-SLF to be problematic in E. coli (32). Thus, we modified the original Hochschild strain KS1 to be tolC− in order to decrease active export of our small molecule. At the low concentrations of Mtx-SLF required for the three-hybrid experiments, however, Mtx was not sufficiently toxic to warrant the thyA− mutation. We introduced the tolC− mutation into KS1 via a P1vir transduction from strain SK037 (32). We call this test strain V674E. Transformation of the plasmids bearing the various λcI and αNTD fusion proteins into V674E yielded the final experimental strains.

The molecular biology performed for the preparation of the strain is described below.

General methods. Restriction enzymes, Vent DNA polymerase and T4 DNA ligase were purchased from New England Biolabs. The dNTPs used in the Polymerase Chain Reation (PCR) were purchased from Pharmacia Biotech. Oligonucleotides were purchased from The Great American Gene Company (www.geneco.com). The bacto-agar, tryptone-peptone and bacto-yeast extract were purchased from DIFCO. Falcon 14 mL culture tubes were used for growing bacteria. Corning Costar 96-well plates with V-shaped wells used for growing the bacteria for solid media plate assays. The phrog used to transfer cells into 96-well plates or onto petri plates containing agar media was purchased from Dan-Kar Corp. (Wilmington, Mass.). 5-Bromo-4-chloro-3-indolyl-β-D-galactopyranoside (X-gal) for the plate assays was purchased from Diagnostic Chemicals (Oxford, Conn.). o-Nitrophenyl-β-D-galactopyranoside (ONPG) for the liquid assays was purchased from Sigma. Methotrexate was from the National Cancer Institutes (NCI). All other chemicals were purchased from Aldrich or Sigma. All aqueous solutions were made with distilled water prepared from a Milli-Q Water Purification System. For Polymerase Chain Reaction (PCR), a MJ Research PTC-200 Pellier Thermal Cycler was employed. The transformation of E. coli was carried out by electroporation using a Bio-Rad E. coli Pulser. UV/Vis spectra and absorbances were taken using a Perkin-Elmer Lambda 6 Spectraphotometer. Restriction digests were carried out as recommended by New England Biolabs. Sequencing of the receptor domains of all plasmids constructed was performed by Gene Wiz (New York, N.Y.). All other standard molecular biology techniques were carried out essentially as described (33–35).

The bacterial two-hybrid plasmids, pACλcI32, pBRαLN, pACLGF2, and pBRαGal11$^P$, and E. coli strain KS1 were obtained (8,21). P1vir and E. coli strain SK037 were obtained (32); and plasmid pJG-FKBP12 was obtained (2).

Construction of λcI-FKBP12 and αNTD-DHFR Protein Chimeras.

The gene encoding dihydrofolate reductase (DHFR) from E. coli was subcloned from plasmid pMW102eDHFR to pBRαLN (7,26). A 531 bp NotI to BamHI fragment was prepared by polymerase chain reaction (PCR) from pMW102eDHFR (26) using the primers 5'-ACT TCA GGT GCG GCC GCA GGC TCG GGC GGC TCG GGC GGC GGA GTG CAG GTG GAA AC-3' (5' primer VWC482, flanked by a NotI site (bold and a italicized) and a Gly-Ser-Gly-Gly-Ser-Gly-Gly linker) (SEQ ID NO:1), and 5'-TGT ATC AAC GGA TCC TTA ATG GTG ATG GTG ATG GTG CGA GCC GAA TTC TTC CAG TTT TAG AA-3' (3' primer VWC487, flanked by a BamHI site (bold and a italicized) and a 6 His tag followed by a stop codon) (SEQ ID NO:2). This fragment was inserted between the NotI site and the BamHI site in pBRαLN to give to pBRαLNeDHFR. The region generated by PCR was verified by DNA sequencing using primers VWC628, 5'-CTG GCT GAA CAA CTG GAA GC (SEQ ID NO:3), and VWC629, 5'-ATA TAG GCG CCA GCA ACC GC (SEQ ID NO:4).

The gene encoding FKBP12 was subcloned from plasmid pJG-FKBP12 to pACλcI32. A 384 bp Not I to Asc I fragment was prepared by polymerase chain reaction (PCR) from plasmid pJG-FKBP12 using the primers 5'-ACT TCA GGT GCG GCC GCA GGC TCG GGC GGC TCG GGC GGC GGA GTG CAG GTG GAA AC-3' (5' primer VWC611, flanked by a NotI site (bold and a italicized) and a Gly-Ser-Gly-Gly-Ser-Gly-Gly linker) (SEQ ID NO:5), and 5'-TGT ATC AAC GGC GCG CCT TAA TGG TGA TGG TGA TGG TGC GAG CCG AAT TCT TCC AGT TTT AGA A-3' (3' primer VWC612, flanked by a AscI site (underlined) and a 6 His tag followed by a stop codon). (SEQ ID NO:6). This fragment was inserted between the NotI site and the AscI site in plasmid pACλcI32 to give pACλcIFKBP12. The region amplified by PCR was verified by DNA sequencing using primers VWC626, 5'-CCC AAT GAT CCC ATG CAA TG, (SEQ ID NO:7), and VWC627, 5'-GCG CTT CGT TAA TAC AGA TG (SEQ ID NO:8), Construction of bacterial strains. (35,36) Strain V674E was made from KS1 via a P1vir transduction from SK037 essentially as described.[14] Incubation times were increased to 30 minutes for infection and 60 minutes after addition of citrate in order to accommodate slower growing times for the mutated strain. The infected cells are then plated on LB plates containing 12 μg/mL tetracycline and 20 mM sodium citrate and incubated at 37° C. overnight. In addition, the positive transductants are verified by streak purification on an LB plate with 12 μg/mL tetracycline, 100 μg/mL kanamycin, and 20 mM sodium citrate to give strain V674E.

Electrocompetent cells of strain V674E were made by standard methods (35); however, the transformation efficiency of this strain is low ($10^6$–$10^7$) due to the tolC− mutation. Using standard methods, both the pACλcI32 and the pBRαLN plasmids or appropriate derivatives were transformed into the strain. Transformants were grown on LB with 100 μg/mL ampicillin and 6 μg/mL chloramphenicol. Note: Chloramphenicol is also a substrate for tolC so levels above 8 μg/mL significantly impair growth and viability of tolC− strains. In addition MacConkey plates can't be used because MacConkey media is toxic to strains bearing a tolC− mutation.

LacZ assays. (7,20,35) The bacterial strains were stored as 20% glycerol stocks in 96-well plates at −80° C. To do the plate assay, the bacterial strains were first phroged to LB liquid media containing 100 μg/mL ampicillin and 6 μg/mL chloramphenicol in a 96-well plate and then incubated in a 37° C. shaker overnight. These saturated cultures were used to innoculate a second 96-well plate containing fresh LB liquid media with 100 µg/mL ampicillin, 6 µg/mL chloramphenicol, and 0.5 mM IPTG using the phrog. These cultures were grown at 37° C. shaking at 240 rpm for 4–5 hours until the cultures were just beginning to be turbid. These cultures were then phrogged to X-gal plates and X-gal plates with varying concentrations of Mtx-SLF and incubated at 37° C. The X-gal plates are LB solid media plates containing 40 µg/mL X-gal, 0.5 mM IPTG, 0.5 tPEG (a β-galactosidase inhibitor), 100 µg/mL ampicillin and 6 µg/mL chloramphenicol. X-gal hydrolysis was first visible at about 8 hours and increased until about 18 hours of growth at which point it appeared to reach a maximum.

For the liquid assays, the strains were incubated overnight in LB liquid media containing 100 µg/mL ampicillin, 6 µg/mL chloramphenicol, and 0.5 mM IPTG overnight. These cultures were used to innoculate 1000 fold into LB liquid media containing 100 µg/mL ampicillin, 6 µg/mL chloramphenicol, 0.5 mM IPTG, and small molecule (per concentration indicated in each experiment) and grown to a final $OD_{600}$ of 0.4-0.6 in a 37° C. shaker which took about 5 hours. No tPEG is used in the liquid assays in order to get a true quantization of the transcription. Then, the protocol from Miller was followed exactly using 0.1 mL cell lysate for the assay (35).

Part III—Screening

Figure 3:
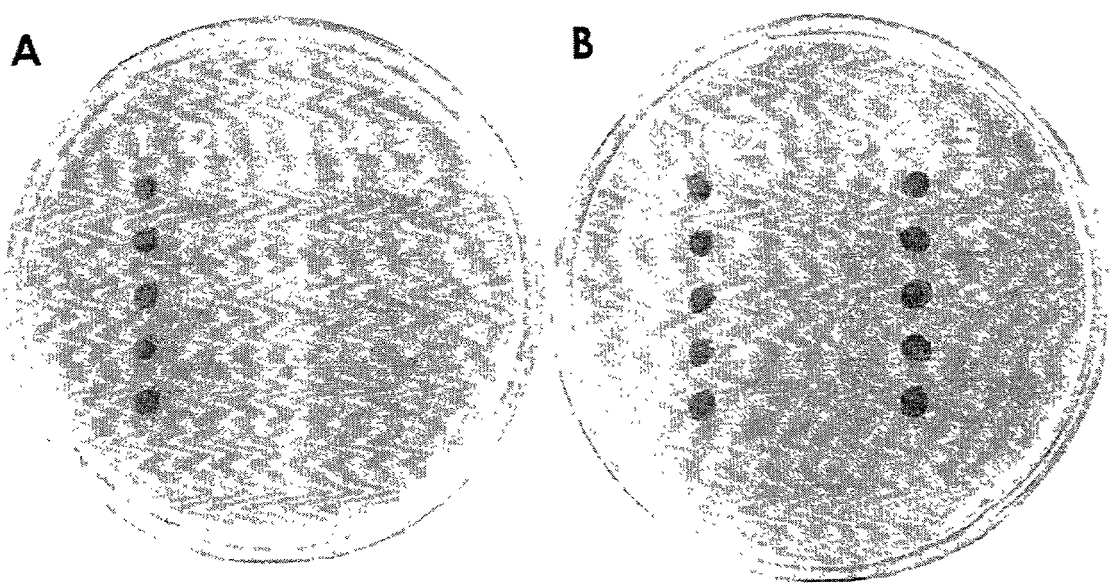
FIG. 3. β-Galactosidase assays establish that transcriptional activation is small-molecule dependent in the bacterial three-hybrid system. X-Gal indicator plates are shown for the different constructs used to verify the three-hybrid system. Each column corresponds to strain V674E bearing plasmids expressing λcI and αNTD fusion proteins involved in the RNA polymerase two- and three-hybrid assays: 1, λcI-Gal4, αNTD-Gal11$^P$; 2, λcI, αNTD; 3, λcI-FKBP12, αNTD; 4, λcI-FKBP12, αNTD-DHFR; 5, λcI, αNTD-DHFR. 1 is the Gal4-Gal11$^P$ direct protein-protein interaction used as a positive control. 2, 3, and 5 lack both of the necessary receptor proteins to test the necessity of all three components for transcriptional activation. Plate A contains no Mtx-SLF; and plate B, 10 µM Mtx-SLF. The plates are LB solid media containing 40 mg/mL X-Gal, 0.5 mM IPTG, 0.5 mM tPEG, 100 mg/mL ampicillin, and 6 mg/mL chloramphenicol.

Using standard β-galactosidase assays on plates (35), we established that Mtx-SLF activates transcription of the lacZ reporter gene in E. coli strain V674E. For the plate assays, Amid-log phase liquid cultures of the strains were transferred to a luria broth (LB) plate containing Mtx-SLF, 5-bromo-4-chloro-3-indolyl-β-D-galactoside (X-gal), isopropyl-β-D-thiogalactopyranoside (IPTG), phenylethyl-β-D-thiogalactoside (tPEG, a β-galactosidase inhibitor), and the appropriate antibiotics. The plates were then incubated for 18 hours at 37° C. The concentrations of Mtx-SLF were varied between 0.1 µM and 10 µM (not all shown). On plates containing Mtx-SLF, we observed a substantial increase in the levels of β-galactosidase synthesis over those due to basal transcription (FIG. 3). Importantly, this increase is dependent on both DHFR and FKBP12 and correlates with the concentration of Mtx-SLF in the plate media. Also, it is interesting to note that at 10 µM Mtx-SLF the levels of small-molecule induced transcription in the three-hybrid strain appears to be greater than those induced by the direct protein-protein interaction in the two-hybrid control.

Figure 4:
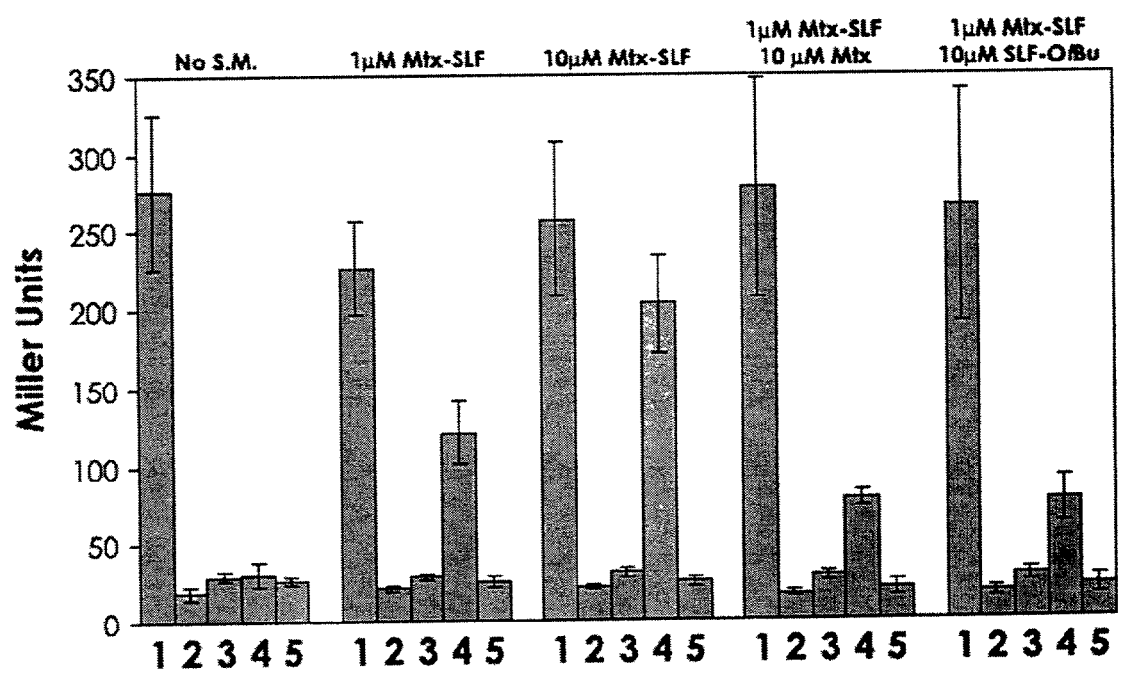
FIG. 4. The levels of small-molecule induced transcriptional activation were quantified using liquid lacZ assays. The strains here correspond exactly to those in FIG. 2 and are used in liquid ONPG assays where the levels of transcriptional activation can be quantitated based on the amount of reporter protein, b-galactosidase, which is produced. The strains are V674E bearing plasmids encoding λcI and αNTD fusion proteins: 1, λcI-Gal4, αNTD-Gal11$^P$; 2, λcI, αNTD; 3, λcI-FKBP12, αNTD; 4, λcI-FKBP12, αNTD-DHFR; 5, λcI, αNTD-DHFR. The strains were assayed in triplicate from three transformants and standard deviations are shown. The strains are grown in LB with 0.5 mM IPTG, 100 µg/mL ampicillin, 6 µg/mL chloramphenicol, and small molecules at the indicated concentration. 1 is the Gal4-Gal11$^P$ direct protein-protein interaction Mtx-SLF independent positive control. Only 4 contains both receptor proteins for Mtx-SLF as the other strains lack either one or both of the receptor proteins. The last two small-molecule concentrations are competition assays in which an excess of one of the ligands for the receptor proteins was used to compete out the positive signal due to the three-hybrid system.
Figure 5:
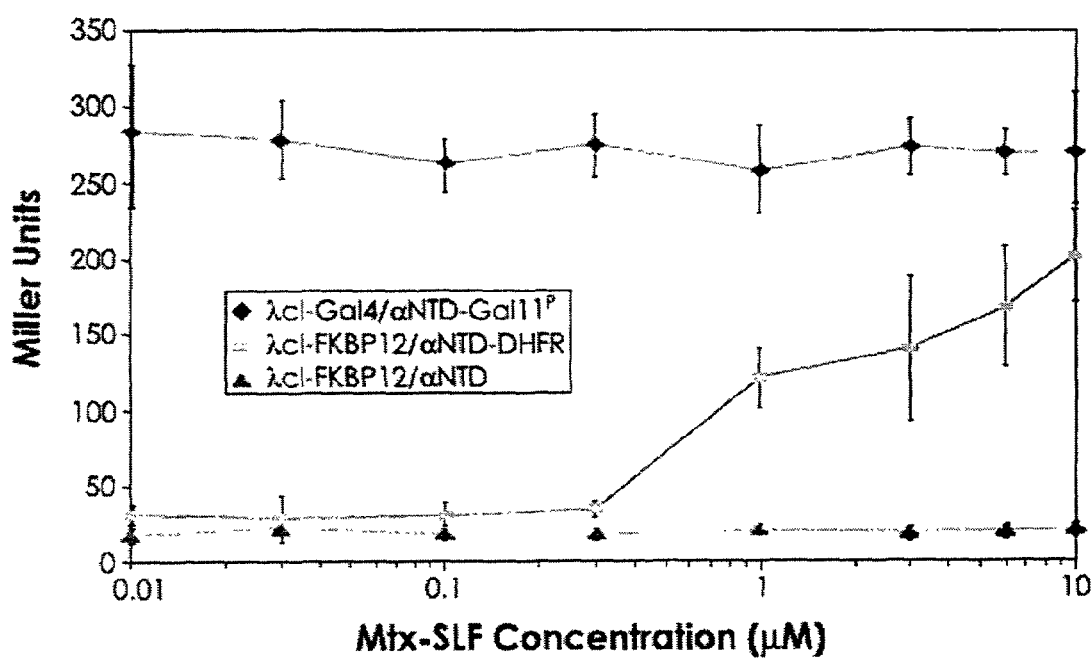
FIG. 5. The levels of transcriptional activation depend on Mtx-SLF concentration in the bacterial three-hybrid system. The concentrations of Mtx-SLF in the media were varied, and the levels of lacZ transcription were quantitated in liquid culture using ONPG. The strains are V674E expressing the following λcI_p and αNTD fusion proteins: (♦), λcI-Gal4, αNTD-Gal11^p (a direct protein-protein interaction); (■), λcI-FKBP12, αNTD (a negative control); and (▲), λcI-FKBP12, αNTD-DHFR (the three-hybrid system). The rate of ONPG hydrolysis was measured in triplicate from three different transformants after growth in LB media containing 0.5 mM IPTG, 100 μg/mL ampicillin, 6 μg/mL chloramphenicol, and Mtx-SLF at the indicated concentrations. The standard deviation for each data point is also shown.

These X-gal plate results were confirmed using more quantitative liquid β-galactosidase assays. The liquid assays were carried out essentially as originally described by Miller (35). Overnight cultures were used to innoculate fresh LB media containing Mtx-SLF, IPTG, and the appropriate antibiotics. These cultures were grown, lysed, and assayed for β-galactosidase activity using o-nitrophenyl-β-D-galactopyranoside (ONPG), a chromogenic substrate for β-galactosidase. We once again observed small-molecule dependent transcriptional activation (FIG. 4). Cells expressing λcI-FKBP12 and αNTD-DHFR showed 6-fold activation at 1 µM and 10-fold activation at 10 µM Mtx-SLF relative to cells expressing only λcI and αNTD. For comparison, the levels of transcription in cells expressing λcI-Gal4 and (αNTD-Gal11$^P$ are 13-fold those of cells with λcI and αNTD and both are unaffected by the concentration of Mtx-SLF in the media. As seen in FIG. 5, the levels of transcriptional activation in the three-hybrid system correlate with the concentration of Mtx-SLF in the media. We begin to see transcriptional activation at 0.3 µm Mtx-SLF, and the levels of activation are still increasing at 10 µM Mtx-SLF. At higher concentrations, Mtx-SLF begins to be toxic to the E. coli cells. Interestingly, at 10 µM Mtx-SLF, the levels of transcriptional activation in the three-hybrid strain approach those in the two-hybrid strain. We attribute this sensitivity to the picomolar affinity of the Mtx/DHFR interaction, although this interpretation has not been proven. Again several independent controls establish that transcriptional activation indeed requires both halves of Mtx-SLF (FIG. 4). Neither Mtx, SLF, nor a combination of the two affects the levels of transcription in the three-hybrid system. At 1 µM Mtx-SLF, a 10-fold excess of either Mtx or the tert-butyl ester of SLF decreased the levels of transcription to about half that with 1 µM Mtx-SLF alone. Deletion of either DHFR or FKBP12 from the λcI-FKBP12 and αNTD-DHFR fusion proteins drops the levels of small-molecule induced transcriptional activation to the background levels observed with only λcI and αNTD.

Discussion

The bacterial small-molecule three-hybrid system described here provides a robust platform for high-throughput assays based on protein-small-molecule interactions. The Mtx-SLF heterodimeric ligand can be prepared readily and gives a strong transcription readout in the E. coli RNA polymerase three-hybrid system. Notably, the levels of transcriptional activation with the Mtx-SLF three-hybrid system are comparable to those with the Gal4-Gal11$^P$ interaction, despite the fact that one non-covalent interaction has been replaced with two. This result may speak to the importance of the particularly high affinity between Mtx and DHFR.

By adapting bacteria to allow for the use of the Mtx/DHFR interaction, the described three-hybrid system that uses Mtx/DHFR is far superior to previous bacterial systems of any type. For example, while it is a different system and designed for different purpose, the system described in (9) provides a context in which the described three-hybrid system based on Mtx/DHFR can be analyzed. The concentrations of small molecule in (9) vary between 50 and 350 uM with 250 uM being the first concentrations at which activity is conclusive. The described Mtx/DHFR system does not need higher than 10 uM and results can be detected absolutely at concentrations below 1 uM. In addition, the described Mtx/DHFR system shows a 10-fold increase in signal upon addition of small molecules whereas in (9) shows a signal to noise ratio of at most 1.25. In fact, the writers of (9) admitted that screening a library would be very difficult with their system, as shown by the fact that when screening a library for activity, they obtain 6 false positives and only a single true positive hit. In addition, the system described in (9) requires several different fluorescent dyes in order to maintain signal stability. Thus, the described bacterial three-hybrid system using Mtx/DHFR is far superior for screening libraries because of the far lower concentrations of small molecule requirements due to much stronger interactions, as well as a vastly improved signal to noise ratio.

Three-hybrid systems provide an in vivo alternative to affinity chromatography that can be used to evolve proteins that recognize a particular small molecule, to screen a library of small molecules based on binding to a particular protein, or to screen cDNA libraries to find the protein targets of drugs or to classify proteins based on their small-molecule interactions. Because of the high transformation efficiency and rapid doubling time of E. coli, this system should increase the number of proteins that can be tested in three-hybrid assays by several orders of magnitude compared with yeast systems. A bacterial assay should be particularly advantageous in molecular evolution experiments where on the order of $10^8$ variants may be necessary to alter protein function. Based on our results, we believe Mtx will provide a versatile anchor for presenting a variety of different small molecules.

The yeast three-hybrid assay provided a method for in vivo affinity chromatography that greatly simplifies protein identification and amplification at the end of affinity panning. The bacterial system described here should increase the number of protein variants that can be assayed by several orders of magnitude.

BIBLIOGRAPHY

1. S. Fields, O. Song, *Nature* 1989, 340, 245–246.
2. U.S. Pat. No. 5,928,868, and Licitra, Edward J., et al., *PNAS, USA* 93, 1996, 93, 12817–12821.
3. U.S. Pat. No. 5,468,614, and Yang et al., *Nucleic Acid Research* 1995, 23, 1152–1156.
4. D. Spencer, T. Wandless, S. Schreiber, G. Crabtree, *Science* 1993, 262, 1019–1024.
5. M. Farrar, J. Alberola-Ila, R. Perlmutter, *Nature* 1996, 383, 178–181.
6. J. Amara, T. Clackson, V. Rivera, T. Guo, T. Keenan, S. Natesan, R. Pollock, W. Yang, N. Courage, D. Holt, M. Gilman, *Proc. Natl. Acad. Sci. USA* 1997, 94, 10618–10623.
7. H. Lin, W. Abida, R. Sauer, V. Cornish, *J. Am. Chem. Soc.* 2000, 122, 4247–4248.
8. J. Hu, M. Kornacker, A. Hochschild, *Methods* 2000, 20, 80–94 and references within.
9. S. Firestine, F. Salinas, A. Nixon, S. Baker, S. Benkovic, *Nat. Biotechnol.* 2000, 18, 544–547.
10. S. Kopytek, R. Standaert, J. Dyer, J. Hu, *Chem. Biol.* 2000, 7, 313–321.
11. J. Bolin; Filman, D.; Matthews, D.; Hamlin, R.; Kraut, J. *J. Biol. Chem.* 1982, 257, 13663–13672.
12. T. Huang; Barclay, B.; Kalman, T.; vonBorstel, R.; Hastings, P. *Gene* 1992, 121,167–171.
13. J. Kralovec; Spencer, G.; Blair, A.; Mammen, M.; Singh, M.; Ghose, T. *J. Med. Chem.* 1989, 32, 2426–2431.
14. J. March, *Advanced Organic Chemistry* (1985) pub. John Wiley & Sons Inc.
15. H H. House, *Modern Synthetic Reactions* (1972) pub.Benjamin Cummings.
16. S. Dove, J. Joung, A. Hochschild, *Nature* 1997, 386, 627–630.
17. S. Michnick, I. Remy, F. Campbell-Valois, A. Vallee-Belisle, J. Pelletier, *Methods Enzymol.* 2000, 238, 208–230.
18. G. Karimova, J. Pidoux, A. Ullmann, D. Ladant, *Proc. Natl. Acad. Sci. USA* 1998, 95, 5752–5756.
19. T. Ozawa, S. Nogami, M. Sato, Y. Ohya, Y. Umezawa, *Anal. Chem.* 2000, 72, 5151–5157.
20. S. Dove, F. Huang, A. Hochschild, *Proc. Natl. Acad. Sci. USA* 2000, 97, 13215–13220.
21. S. Dove, A. Hochschild, *Genes & Dev.* 1998, 12, 745–754.
22. J. Alam and Cook, J. L., Anal. Biochem. 188: 245–254, (1990).
23. N. Rosenthal, *Methods Enzymo.* 152: 704–720 (1987).
24. A. Shiau and Smith, J. M., *Gene* 67: 295–299 (1988).
25. S. Benkovic, C. Fierke, A. Naylor, *Science* 1988, 239, 1105–1110.
26. W. Abida, B. Carter, E. Althoff, H. Lin, V. Cornish, submitted for publication 2002.
27. T. Keenan, D. R. Yaeger, N. L. Courage, C. T. Rollins, M. E. Pavone, V. M. Rivera, W. Yang, T. Guo, J. F. Amara, T. Clackson, M. Gilman, D. A. Holt, *Bioorg. Med. Chem.* 1998, 6, 1309–1335.
28. D. Holt, J. Luengo, D. Yamashita, H. Oh, A. Konialan, H. Yen, L. Rozamus, M. Brandt, M. Bossard, M. Levy, D. Eggleston, J. Liang, L. Schultz, T. Stout, J. Clardy, *J. Am. Chem. Soc.* 1993, 115, 9925–9938.
29. T. Clackson, *Curr. Opin. Chem. Biol.* 1997, 1, 210–218.
30. B. Hart, W. Haile, N. Licato, W. Bolanowska, J. McGuire, J. Coward, *J. Med. Chem.* 1996, 39, 56–65.
31. L. Liu, R. Tanke, M. Miller, *J. Org. Chem.* 1986, 51, 5332–5337.
32. S. Kopytek, J. Dyer, G. Knapp, J. Hu, *Antimicrob. Agents Chemother.* 2000, 44, 3210–3212.
33. F. Ausubel, R. Brent, R. Kingston, D. Moore, J. Seidman, J. Smith, K. Struhl, *Current Protocols in Molecular Biology*, John Wiley & Sons, New York, 1995.
34. J. Sambrook, E. Fritsch, T. Maniatis, *Molecular Cloning a Laboratory Manual,* 2nd ed., Cold Spring Harbor Laboratory Press, Plainview, N.Y., 1989.
35. J. H. Miller, *A Short Course in Bacterial Genetics : A Laboratory Manual and Handbook for Escherichia Coli and Related Bacteria*, Cold Spring Harbor Laboratory Press, Plainview, N.Y., 1992.
36. P1 Transduction, http://hulab.tamu.edu/Protocalls/Transduction/P1vir % 20Transduction.html.
37. D. Ladant and G. Karimova, Genetic systems for analyzing protein-protein interactions in bacteria, Res. Microbiol., 2000, 151:711–720.
38. J. Pelletier, F.-X. Campbell-Valois, and S. Michnick, Oligomerization domain-directed reassembly of active dihydrofolate reductase from rationally designed fragments, *PNAS USA*, October 1998, 95:12141–12146.

What is claimed is:

1. A method for identifying a molecule that binds a known target receptor in a bacterial cell from a pool of candidate molecules, comprising:
   (a) forming a dimeric molecule by covalently bonding each molecule in the pool of candidate molecules to a ligand capable of selectively binding to a receptor;
   (b) introducing the dimeric molecule into a bacterial cell culture comprising bacterial cells that express a first fusion protein which comprises the known target receptor domain against which the candidate molecule is screened, a second fusion protein which comprises the receptor domain to which the ligand selectively binds, and a reporter gene wherein expression of the reporter gene is conditioned on the proximity of the first fusion protein to the second fusion protein;
   (c) permitting the dimeric molecule to bind to the first fusion protein and to the second fusion protein, bringing the two fusion proteins into proximity so as to activate the expression of the reporter gene;
   (d) selecting the bacterial cell that expresses the reporter gene; and
   (e) identifying the small molecule that binds the known target receptor.

2. A method for identifying an unknown target receptor to which a known molecule is capable of binding in a bacterial cell, comprising:
   (a) providing a dimeric molecule having a first ligand which has a specificity for the unknown target receptor covalently bonded to a second ligand capable of selectively binding to a receptor;
   (b) introducing the dimeric molecule into a bacterial cell which expresses a first fusion protein which comprises the unknown target receptor domain, a second fusion protein which comprises the receptor domain to which the second ligand selectively binds, and a reporter gene wherein expression of the reporter gene is conditioned on the proximity of the first fusion protein to the second fusion protein;
   (c) permitting the dimeric molecule to bind to the first fusion protein and to the second fusion protein so as to activate the expression of the reporter gene;
   (d) selecting which bacterial cell expresses the unknown target receptor; and
   (e) identifying the unknown target receptor.

3. A transgenic bacterial cell comprising
   (a) a dimeric small molecule which comprises a methotrexate moiety covalently linked to a moiety capable of binding a receptor domain;
   (b) nucleotide sequences which upon transcription encode
      i) a first fusion protein comprising a DHFR domain and a first fragment of an enzyme, and
      ii) a second fusion protein comprising the receptor domain and a second fragment of the enzyme,
   wherein activity of the enzyme is conditioned on the proximity of the first fragment of the enzyme to the second fragment of the enzyme.

4. A method for identifying a molecule that binds a known target receptor in a bacterial cell from a pool of candidate molecules, comprising:
   (a) forming a dimeric molecule by covalently bonding each molecule in the pool of candidate molecules to a methotrexate moiety;
   (b) introducing the dimeric molecule into a bacterial cell culture comprising bacterial cells that express a first fusion protein which comprises the known target receptor domain against which the candidate molecule is screened, and a first fragment of an enzyme, and a second fusion protein which comprises a DHFR receptor domain and a second fragment of the enzyme;
   (c) permitting the dimeric molecule to bind to the first fusion protein and to the second fusion protein, bringing the first fragment and the second fragment of the enzyme in to proximity so as to reconstitute the activity of the enzyme;
   (d) selecting the bacterial cell that exhibits the activity of the enzyme; and
   (e) identifying the small molecule that binds the known target receptor.

5. A method for identifying an unknown target receptor to which a known molecule is capable of binding in a bacterial cell, comprising:
   (a) providing a dimeric molecule having a first ligand which has a specificity for the unknown target receptor covalently bonded to a methotrexate moiety;
   (b) introducing the dimeric molecule into a bacterial cell which expresses a first fusion protein which comprises the unknown target receptor domain, and a first fragment of an enzyme, and a second fusion protein which comprises a DHFR receptor domain and a second fragment of the enzyme;
   (c) permitting the dimeric molecule to bind to the first fusion protein and to the second fusion protein, bringing the first fragment and the second fragment of the enzyme in to proximity so as to reconstitute the activity of the enzyme;
   (d) selecting the bacterial cell that exhibits the activity of the enzyme; and
   (e) identifying the unknown target receptor.

6. The method of claim 1, wherein the steps (b)–(e) of the method are iteratively repeated in the presence of a preparation of random small molecules for competitive binding with the screening molecule so as to identify a molecule capable of competitively binding the known target receptor.

7. The method of claim 1, wherein the dimeric molecule is obtained from a combinatorial library.

8. The method of claim 1, wherein the dimeric molecule comprises a ligand capable of selectively binding to a receptor with a $IC_{50}$ of less than 100 µM.

9. The method of claim 8, wherein the dimeric molecule comprises a ligand capable of selectively binding to a receptor with a $IC_{50}$ of less than 100 nM.

10. The method of claim 9, wherein the dimeric molecule comprises a ligand capable of selectively binding to a receptor with a $IC_{50}$ of less than 1 nM.

11. The method of claim 1, wherein the dimeric molecule comprises a methotrexate moiety, FK506 moiety, a tetracycline moiety, or a cephem moiety.

12. The method of claim 1, wherein the dimeric molecule comprises a methotrexate moiety.

13. The method of claim 1, wherein dimeric molecule comprises an FK506 analog having the structure:

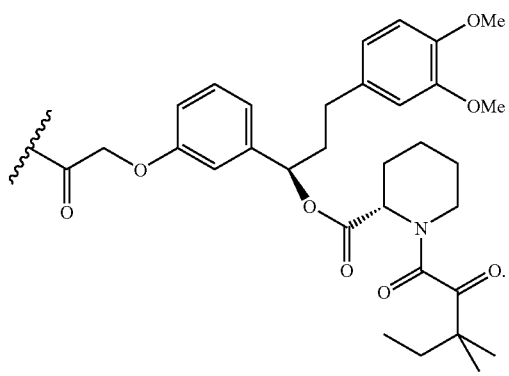

14. The method of claim 1, wherein the first fusion protein further comprises a DNA binding domain, and the second fusion protein further comprises a transcription activation domain.

15. The method of claim 1, wherein the first fusion protein further comprises a transcription activation domain, and the second fusion protein further comprises a DNA binding domain.

16. The method of claim 14 or 15, wherein the transcription activation domain is αNTD.

17. The method of claim 14 or 15, wherein the DNA-binding domain is λcI, AraC, LexA, Gal4, or zinc fingers.

18. The method of claim 1, wherein the first or the second fusion protein comprises a receptor domain of dihydrofolate reductase ("DHFR"), glucocorticoid receptor, FKBP12, FKBP mutantz, tetracycline repressor, or a penicillin binding protein.

19. The method of claim 18, wherein the DHFR is the *E. coli* DHFR ("eDHFR").

20. The method of claim 1, wherein the first fusion protein is DHFR-λcI or FKBP12-λcI.

21. The method of claim 1, wherein the second fusion protein is DHFR-αNTD or FKBP12-αNTD.

22. The method of claim 1, wherein the reporter gene is Lac Z, araBAD, aadA, his3, β-lactamase, GFP, luciferase, TetR, KanR, or Cm.

23. The method of claim 22, wherein the reporter gene is Lac Z.

24. The method of claim 2, wherein the unknown target receptor is encoded by a DNA from the group consisting of genomicDNA, cDNA and syntheticDNA.

25. The method of claim 2, wherein the steps (b)–(e) of the method are iteratively repeated so as to identify the unknown target receptor.

26. The method of claim 2, wherein the dimeric molecule comprises a ligand capable of selectively binding to a receptor with a $IC_{50}$ of less than 100 µM.

27. The method of claim 2, wherein the dimeric molecule comprises a ligand capable of selectively binding to a receptor with a $IC_{50}$ of less than 100 nM.

28. The method of claim 2, wherein the dimeric molecule comprises a ligand capable of selectively binding to a receptor with a $IC_{50}$ of less than 1 nM.

29. The method of claim 2, wherein the dimeric molecule comprises a methotrexate moiety, FK506 moiety, a teracycline moiety, or a cephem moiety.

30. The method of claim 2, wherein the dimeric molecule comprises a methotrexate moiety.

31. The method of claim 2, wherein the dimeric molecule is an FK506 analog having the structure:

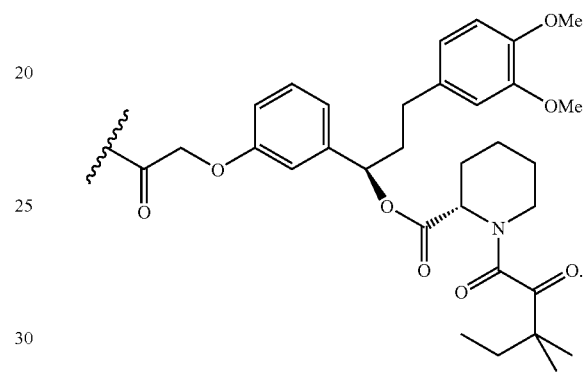

32. The method of claim 2, wherein the first fusion protein further comprises a DNA binding domain, and the second fusion protein further comprises a transcription activation domain.

33. The method of claim 2, wherein the first fusion protein further comprises a transcription activation domain, and the second fusion protein further comprises a DNA binding domain.

34. The method of claim 32 or 33, wherein the transcription activation domain is αNTD.

35. The method of claim 32 or 33, wherein the DNA-binding domain is λcI, AraC, LexA, Gal4, or zinc fingers.

36. The method of claim 2, wherein the first or the second fusion protein comprises a receptor domain of dihydrofolate reductase ("DHFR"), glucocorticoid receptor, FKBP12, tetracycline repressor, or a penicillin binding protein.

37. The method of claim 36, wherein the DHFR is the *E. coli* DHFR ("eDHFR").

38. The method of claim 2, wherein the first fusion protein is DHFR-λcI or FKBP12-λcI.

39. The method of claim 2, wherein the second fusion protein is DHFR-αNTD or FKBP12-αNTD.

40. The method of claim 2, wherein the reporter gene is Lac Z, araBAD, aadA, his3, β-lactamase, GFP, luciferase, TetR, KanR, or Cm.

41. The method of claim 40, wherein the reporter gene is Lac Z.

42. A process for screening a chemical library for a molecule that binds a known target receptor, comprising providing a chemical library, providing a bacterial cell that expresses the known target receptor as a part of a fusion protein, and identifying the molecule that binds the known target receptor in the bacterial cell by the method of claim 1.

* * * * *